(12) United States Patent
Parham et al.

(10) Patent No.: US 8,859,111 B2
(45) Date of Patent: Oct. 14, 2014

(54) MATERIALS FOR ORGANIC ELECTROLUMINESCENT DEVICES

(75) Inventors: Amir Hossain Parham, Frankfurt (DE); Susanne Heun, Bad Soden (DE); Esther Breuning, Ober-Ramstadt (DE)

(73) Assignee: Merck Patent GmbH (DE)

( * ) Notice: Subject to any disclaimer, the term of this patent is extended or adjusted under 35 U.S.C. 154(b) by 347 days.

(21) Appl. No.: 13/384,250

(22) PCT Filed: Jun. 18, 2010

(86) PCT No.: PCT/EP2010/003697
§ 371 (c)(1),
(2), (4) Date: Jan. 16, 2012

(87) PCT Pub. No.: WO2011/006574
PCT Pub. Date: Jan. 20, 2011

(65) Prior Publication Data
US 2012/0126179 A1 May 24, 2012

(30) Foreign Application Priority Data

Jul. 14, 2009 (DE) .......................... 10 2009 032 922

(51) Int. Cl.
*H01L 51/54* (2006.01)
*C07C 217/94* (2006.01)
(Continued)

(52) U.S. Cl.
CPC ......... *C09K 11/06* (2013.01); *C09K 2211/1029* (2013.01); *C07C 2103/94* (2013.01); *C07D*
(Continued)

(58) Field of Classification Search
CPC .... C07C 13/72; C07C 49/665; C07C 211/61; C07C 217/94; C07C 43/21; C07C 2103/94; C07D 209/86; C07D 235/20; C07D 241/48; C07D 251/24; C07D 265/38; C07D 333/08; C07D 333/16; C07D 403/10; C07D 471/10; C07F 9/5325; C09K 11/06; C09K 2211/1011; C09K 2211/1014; C09K 2211/1029; C09K 2211/1033; C09K 2211/1044; C09K 2211/1059; C09K 2211/1092; C09K 2211/185; H01L 51/0059; H01L 51/0067; H01L 51/5016; H01L 51/5048; H05B 33/14; C09B 23/14; C09B 57/00; C09B 57/008; C09B 1/00; Y02E 10/549
See application file for complete search history.

(56) References Cited

U.S. PATENT DOCUMENTS 5,840,217 A    11/1998  Lupo et al.
6,476,265 B1   11/2002  Spreitzer et al.
(Continued)

FOREIGN PATENT DOCUMENTS

DE       19804310 A1    8/1999
DE     102004008304 A1  9/2005
(Continued)

OTHER PUBLICATIONS

Machine translation for JP 2009-203176 (publication date Sep. 2009).*

*Primary Examiner* — Dawn L. Garrett
(74) *Attorney, Agent, or Firm* — Drinker Biddle & Reath LLP

(57) ABSTRACT

The present invention relates to 4,4'-substituted spirobifluorenes which are suitable, owing to excellent properties, as functional materials in organic electroluminescent devices. In addition, the present invention relates to a process for the preparation of 4,4'-substituted spirobifluorenes and to the use of these compounds in organic electroluminescent devices.

19 Claims, 1 Drawing Sheet

Figure 1:
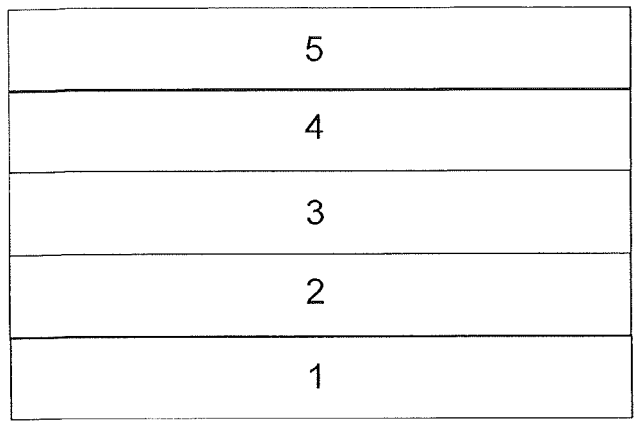

| 5 |
|---|
| 4 |
| 3 |
| 2 |
| 1 |

(51) Int. Cl.
| | |
|---|---|
| C07C 13/72 | (2006.01) |
| C07C 211/61 | (2006.01) |
| C07C 41/30 | (2006.01) |
| C09K 11/06 | (2006.01) |
| C07D 251/24 | (2006.01) |
| C07F 9/53 | (2006.01) |
| C09B 57/00 | (2006.01) |
| C09B 1/00 | (2006.01) |
| H01L 51/00 | (2006.01) |
| C07D 471/10 | (2006.01) |
| C07D 241/48 | (2006.01) |
| C07D 333/16 | (2006.01) |
| H05B 33/14 | (2006.01) |
| C07D 209/86 | (2006.01) |
| C07D 333/08 | (2006.01) |
| C07D 265/38 | (2006.01) |
| C07D 235/20 | (2006.01) |
| C07C 49/665 | (2006.01) |
| C09B 23/14 | (2006.01) |
| C07D 403/10 | (2006.01) |
| C07C 43/21 | (2006.01) |
| H01L 51/50 | (2006.01) |

(52) U.S. Cl.
CPC .... 251/24 (2013.01); *C07F 9/5325* (2013.01); *C09K 2211/1059* (2013.01); *C09B 57/008* (2013.01); *C09K 2211/1044* (2013.01); *C09B 1/00* (2013.01); *H01L 51/0059* (2013.01); *C07C 211/61* (2013.01); *C07D 471/10* (2013.01); *Y02E 10/549* (2013.01); *C07C 217/94* (2013.01); *C07D 241/48* (2013.01); *C07C 13/72* (2013.01); *C07D 333/16* (2013.01); *H05B 33/14* (2013.01); *C07D 209/86* (2013.01); *C07D 333/08* (2013.01); *H01L 51/5016* (2013.01); *C07D 265/38* (2013.01); *H01L 51/5048* (2013.01); *C07D 235/20* (2013.01); *C07C 49/665* (2013.01); *C09K 2211/1014* (2013.01); *H01L 51/0067* (2013.01); *C09B 57/00* (2013.01); *C09K 2211/1033* (2013.01); *C09B 23/14* (2013.01); *C09K 2211/1011* (2013.01); *C07D 403/10* (2013.01); *C09K 2211/1092* (2013.01); *C07C 43/21* (2013.01); *C09K 2211/185* (2013.01); *Y10S 428/917* (2013.01)
USPC ......... 428/690; 428/917; 313/504; 313/506; 585/27; 252/301.16; 564/399; 564/427; 568/633

(56) References Cited

U.S. PATENT DOCUMENTS

| | | | |
|---|---|---|---|
| 7,088,757 B1 * | 8/2006 | Yu et al. | 372/53 |
| 2003/0065190 A1 * | 4/2003 | Spreitzer et al. | 548/134 |
| 2003/0111107 A1 * | 6/2003 | Salbeck et al. | 136/256 |
| 2005/0127826 A1 | 6/2005 | Qiu et al. | |
| 2006/0063027 A1 | 3/2006 | Vestweber et al. | |
| 2006/0134425 A1 * | 6/2006 | Suzuki et al. | 428/411.1 |
| 2007/0170419 A1 | 7/2007 | Gerhard et al. | |
| 2009/0226759 A1 * | 9/2009 | Heun et al. | 428/704 |

FOREIGN PATENT DOCUMENTS

| | | | |
|---|---|---|---|
| JP | 2009-203176 | * | 9/2009 |
| WO | WO-2004/058911 A2 | | 7/2004 |

* cited by examiner

MATERIALS FOR ORGANIC ELECTROLUMINESCENT DEVICES

RELATED APPLICATIONS

This application is a national stage application (under 35 U.S.C. §371) of PCT/EP2010/003697, filed Jun. 18, 2010, which claims benefit of German Application No. 10 2009 032 922.6, filed Jul. 14, 2009.

The present invention relates to 4,4'-substituted spirobifluorenes which are suitable, owing to excellent properties, as functional materials in organic electroluminescent devices. In addition, the present invention relates to a process for the preparation of 4,4'-substituted spirobifluorenes and to the use of these compounds in organic electroluminescent devices.

The general structure of organic electroluminescent devices is described, for example, in U.S. Pat. No. 4,539,507, U.S. Pat. No. 5,151,629, EP 0676461 and WO 98/27136. However, there is still a need for improvement in these devices:

1. The operating lifetime is still short, in particular in the case of blue or green emission, meaning that it has to date only been possible to achieve simple applications commercially.
2. The compounds used are in some cases only sparingly soluble in common organic solvents, which makes purification thereof during synthesis more difficult, but also makes processing of the materials from solution and cleaning of the equipment in the production of the electronic devices more difficult.
3. The materials used, in particular spirobifluorene materials in accordance with the prior art, frequently have low triplet energy. This results in quenching of the emission on combination with materials which emit from the triplet state and thus results in a reduction in efficiency.

JP 2006/256982 and WO 2002/051850 describe partially conjugated spirobifluorene compounds which are linked via the 2,2'-positions of the spirobifluorene units.

DE 19804310 and EP 676461 describe partially conjugated spirobifluorene compounds which are linked via the 2,2',7,7',4,4'-positions of the spirobifluorene units.

In particular, the excellent processability is mentioned as an advantage of these materials. Regarding the electronic properties, however, it is only reported that electroluminescence is observed on application of an adequately high voltage, without commenting on the voltage, efficiency and lifetime.

Although materials are available for organic electroluminescent devices, there continues to be a demand for improved materials which are thermally stable, which result in good efficiencies and at the same time in long lifetimes in organic electronic devices, which give reproducible results in the production and operation of the device and which are readily accessible synthetically. Further improvements are also necessary in hole- and electron-transport materials.

Spirobifluorene materials have major advantages for use in vapour-deposited OLEDs, but also from solution in the film of spirobifluorene polymers or as soluble spirobifluorene molecules, owing to their very good film-formation properties and high glass-transition temperatures. Due to the usual linking (2,2'-position or 2,7-position), however, they always contain a para-linked biphenyl bridge and thus a minimum conjugation, which reduces the adjustability of the band gap. This becomes particularly evident in the case of triarylamine dimers, where in each case two aryl units on one triarylamine are linked in a spiro manner to the second triarylamine unit, which consequently have a smaller band gap than unbridged triarylamines.

Although asymmetrical spiro compounds are known and can be prepared, they are accessible synthetically in good yield and purity only with difficulty.

4,4'-Substitution of spirobifluorenes enables hole and electron conductors, but also emitters, to be linked to the spiro unit without the formation of a para-linked biphenyl bridge and thus the occurrence of the disadvantages mentioned above. This makes, for example, hole-transporting spiro materials possible which do not quench green or blue triplet emission, but, in contrast to the very small triphenylamine or tritolylamine, have good film-formation properties and a higher glass-transition temperature. The same effect can be used for electron conductors, where similar disadvantages of the biphenyl bridge with respect to its triplet energy have been observed. Deep-blue emitters and matrix materials for triplet emitters are likewise possible.

The invention relates to compounds of the following formula I:

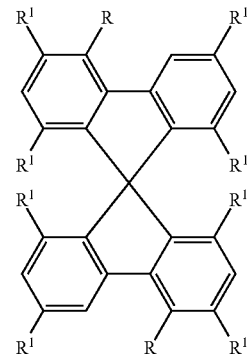

formula I where the symbols used have the following meanings:

R is selected on each occurrence, identically or differently, from the group consisting of F, CN, $NO_2$, $ArNAr_2$, $NAr_2$, $C(=O)Ar$, $ArC(=O)Ar$, $C(=O)R^2$, $P(=O)Ar_2$, $S(=O)Ar$, $S(=O)_2Ar$, $-CR^2=C(R^2)_2$ and a mono- or polycyclic aromatic or heteroaromatic ring system having 5 to 60 aromatic ring atoms, which may be substituted by one or more non-aromatic radicals $R^1$; two radicals Ar here which are bonded to the same nitrogen or phosphorus atom may also be linked to one another by a single bond or a bridge selected from $B(R^2)$, $C(R^2)_2$, $Si(R^2)_2$, $C=O$, $C=NR^2$, $C=C(R^2)_2$, O, S, $S=O$, $SO_2$, $N(R^2)$, $P(R^2)$ and $P(=O)R^2$;

$R^1$ is selected, identically or differently on each occurrence, from the group consisting of H, D, F, Cl, Br, I, OH, CN, a straight-chain alkyl, alkoxy or thioalkoxy group having 1 to 40 C atoms and a branched or cyclic alkyl, alkoxy or thioalkoxy group having 3 to 40 C atoms or an alkenyl or alkynyl group having 2 to 40 C atoms, each of which may be substituted by one or more radicals $R^2$, where one or more non-adjacent $CH_2$ groups may be replaced by $R^2C=CR^2$, $C\equiv C$, $Si(R^2)_2$, $C=O$, $C=S$, $C=NR^2$, $P(=O)(R^2)$, SO, $SO_2$, $NR^2$, O or S and where one or more H atoms may be replaced by D, F, Cl, Br, I, CN or $NO_2$; where, in addition, the respective $R^1$ which is located in the vicinal position to the radical R, in the case where R is an aromatic or heteroaromatic ring system, can be a divalent unit which is linked to the group R;

Ar is on each occurrence, identically or differently, an aromatic or heteroaromatic ring system having 5 to 30 aromatic ring atoms, which may be substituted by one or more radicals $R^1$;

$R^2$ is selected on each occurrence, identically or differently, from the group consisting of H, D, F, CN and an aliphatic, aromatic or heteroaromatic hydrocarbon radical having 1 to 20 C atoms, in which, in addition, one or more H atoms may be replaced by D, F, CN, a straight-chain alkyl, alkoxy or thioalkoxy group having 1 to 40 C atoms or a branched or cyclic alkyl, alkoxy or thioalkoxy group having 3 to 40 C atoms; two or more adjacent substituents $R^2$ here may also be linked to one another by a covalent bond or also, in the case where the $R^2$ involved are aromatic or heteroaromatic hydrocarbon radicals, by one or more divalent aliphatic hydrocarbon units.

A mono- or polycyclic aromatic or heteroaromatic ring system preferably contains 5 to 60, particularly preferably 5 to 40, more preferably 5 to 30, even more preferably 5 to 20, even more preferably 6 to 14 and most preferably 6 to 12, aromatic ring atoms. An aromatic ring system in the sense of this invention contains 6 to 60 C atoms in the ring system. A hetero-aromatic ring system in the sense of this invention contains 1 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which a plurality of aryl or heteroaryl groups may also be connected by a short non-aromatic unit, such as, for example, a C, N or O atom. Thus, for example, systems such as 9,9'-spirobifluorene, 9,9-diaryl-fluorene, triarylamine, diaryl ether, stilbene, benzophenone, etc., are also intended to be taken to mean aromatic ring systems for the purposes of this invention. Likewise, an aromatic or heteroaromatic ring system is taken to mean systems in which a plurality of aryl or heteroaryl groups are linked to one another by single bonds, for example biphenyl, terphenyl or bipyridine.

Examples of the aromatic or heteroaromatic ring systems according to the invention, which may in each case also be substituted by the above-mentioned radicals $R^1$, preferably the non-aromatic representatives of the radical $R^1$, and which may be linked via any desired positions on the aromatic or heteroaromatic ring system, include the following: benzene, naphthalene, anthracene, phenanthrene, pyrene, chrysene, perylene, fluoranthene, naphthacene, pentacene, benzanthracene, benzophenanthrene, dibenzanthracene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-indolocarbazole, cis- or trans-indenocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthroimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

For the purposes of the present invention, a straight-chain, branched or cyclic alkyl group is taken to mean an alkyl, alkenyl or alkynyl group, preferably having 1 to 40 C atoms, more preferably 1 to 20 C atoms, or 3 to 40 C atoms, more preferably 3 to 20 C atoms, respectively. Cyclic alkyl groups can be mono-, bi- or polycyclic alkyl groups. Individual —CH— or —CH$_2$— groups may be replaced by N, NH, O or S. Preference is given to the radicals methyl, ethyl, n-propyl, isopropyl, n-butyl, isobutyl, sec-butyl (1-methylpropyl), tert-butyl, isopentyl, n-pentyl, tert-pentyl (1,1-dimethylpropyl), 1,2-dimethylpropyl, 2,2-dimethylpropyl (neopentyl), 1-ethylpropyl, 2-methylbutyl, n-hexyl, isohexyl, 1,2-dimethylbutyl, 1-ethyl-1-methylpropyl, 1-ethyl-2-methylpropyl, 1,1,2-trimethylpropyl, 1,2,2-trimethylpropyl, 1-ethylbutyl, 1-methylbutyl, 1,1-dimethylbutyl, 2,2-dimethylbutyl, 1,3-dimethylbutyl, 2,3-dimethylbutyl, 3,3-dimethylbutyl, 2-ethylbutyl, 1-methylpentyl, 2-methylpentyl, 3-methylpentyl, cyclopentyl, cyclohexyl, cycloheptyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl and octynyl.

A straight-chain, branched or cyclic alkoxy group or thioalkoxy group is taken to mean an alkyl group as defined above which is bonded to the remainder of the compound via an O or S atom. Preferred alkoxy groups are methoxy, trifluoromethoxy, ethoxy, n-propoxy, i-propoxy, n-butoxy, i-butoxy, s-butoxy, t-butoxy or 2-methylbutoxy.

Aliphatic hydrocarbons according to the invention having 1 to 20 or 3 to 20 carbon atoms are preferably linear, branched or cyclic alkyl groups, alkenyl groups or alkynyl groups, in which one or more carbon atoms may be replaced by O, N or S. In addition, one or more hydrogen atoms may be replaced by fluorine. Examples of aliphatic hydrocarbons having 1 to 20 carbon atoms are the groups mentioned above.

An aromatic or heteroaromatic hydrocarbon preferably contains 5 to 20, more preferably 5 to 10, most preferably 5 or 6, aromatic ring atoms. If the unit is an aromatic unit, it preferably contains 6 to 20, more preferably 6 to 10, most preferably 6, carbon atoms as ring atoms. If the unit is a heteroaromatic unit, it contains 5 to 20, more preferably 5 to 10, most preferably 5, aromatic ring atoms, at least one of which is a heteroatom. The heteroatoms are preferably selected from N, O and/or S. An aromatic or heteroaromatic unit here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, benzothiophene, benzofuran and indole, etc.

Examples according to the invention of the aromatic or heteroaromatic unit are accordingly the groups already mentioned above for the aromatic or heteroaromatic ring system.

If the $R^1$ which is located in the vicinal position to the radical R is a divalent unit which is linked to the group R, the divalent unit is preferably a —C($R^3$)$_2$— unit, where $R^3$ is an aliphatic hydrocarbon radical having 1 to 20, preferably 1 to 10, more preferably 1 to 6 and most preferably 1 to 3, carbon atoms or an aromatic or heteroaromatic hydrocarbon radical having 5 to 20, more preferably 5 to 10 and most preferably 5 or 6, aromatic ring atoms. $R^3$ is in each case particularly preferably, identically or differently, preferably identically, on each occurrence, methyl or phenyl. In this case, the radicals $R^1$ and R together form a divalent unit, which is preferably selected from the following:

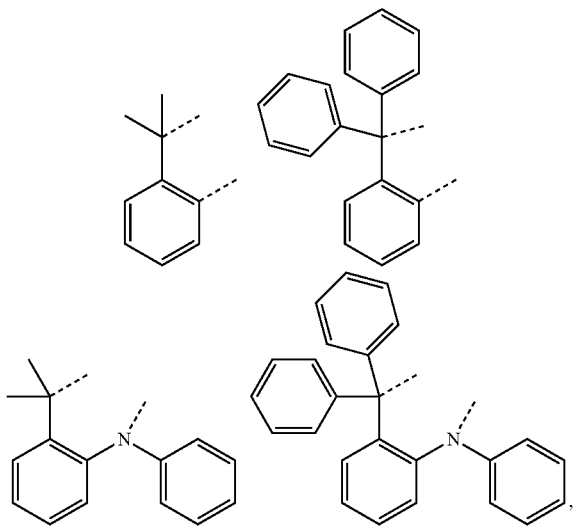

where the dashed lines are intended to represent bonds to the spirobifluorene at the positions where the corresponding R and $R^1$ are drawn in, and where the dashed line on the phenyl group or the dashed line on the nitrogen atom is intended to represent a bond to the atom where R is drawn in as substituent.

In a further embodiment of the present invention, R of the compound of the formula I is preferably in each case selected, independently of one another, from the group consisting of $NAr_2$, $C(=O)R^2$, $CR^2=C(R^2)_2$ and a mono- or polycyclic aromatic or heteroaromatic ring system having 5 to 40 aromatic ring atoms, which may be substituted by one or more non-aromatic radicals $R^1$; where, in addition, two radicals Ar which are bonded to the same nitrogen atom may be linked to one another by a single bond or a bridge selected from $C(R^2)_2$, $C=O$, O, S and $N(R^2)$.

In still a further embodiment of the present invention, R of the compound of the formula I is preferably, independently of one another, $NAr_2$ or a mono- or polycyclic aromatic or heteroaromatic ring system having 5 to 20 aromatic ring atoms. It is more preferred for R to be equal to $NAr_2$ or a mono- or polycyclic heteroaromatic ring system having 5 to 20, more preferably 6 to 12, aromatic ring atoms, where one or more of the ring atoms are nitrogen atoms. In other words, R is an electron-deficient heteroaromatic group. Accordingly, even greater preference is given to a heteroaromatic group having 6 aromatic ring atoms, of which at least one is an N atom, or a heteroaromatic group having 5 aromatic ring atoms, of which at least two are heteroatoms, preferably one thereof is an N atom. Preferred examples thereof are: pyridine, pyrazine, pyrimidine, pyridazine, 1,2,4-triazine, 1,3,5-triazine, quinoline, isoquinoline, pyrazole, imidazole, benzimidazole, thiazole, benzothiazole, oxazole, benzoxazole. R is most preferably a substituted or unsubstituted 1,3,5-triazine or benzimidazole.

In still a further embodiment of the present invention, R of the compound of the formula I is preferably selected from the group consisting of the following radicals:

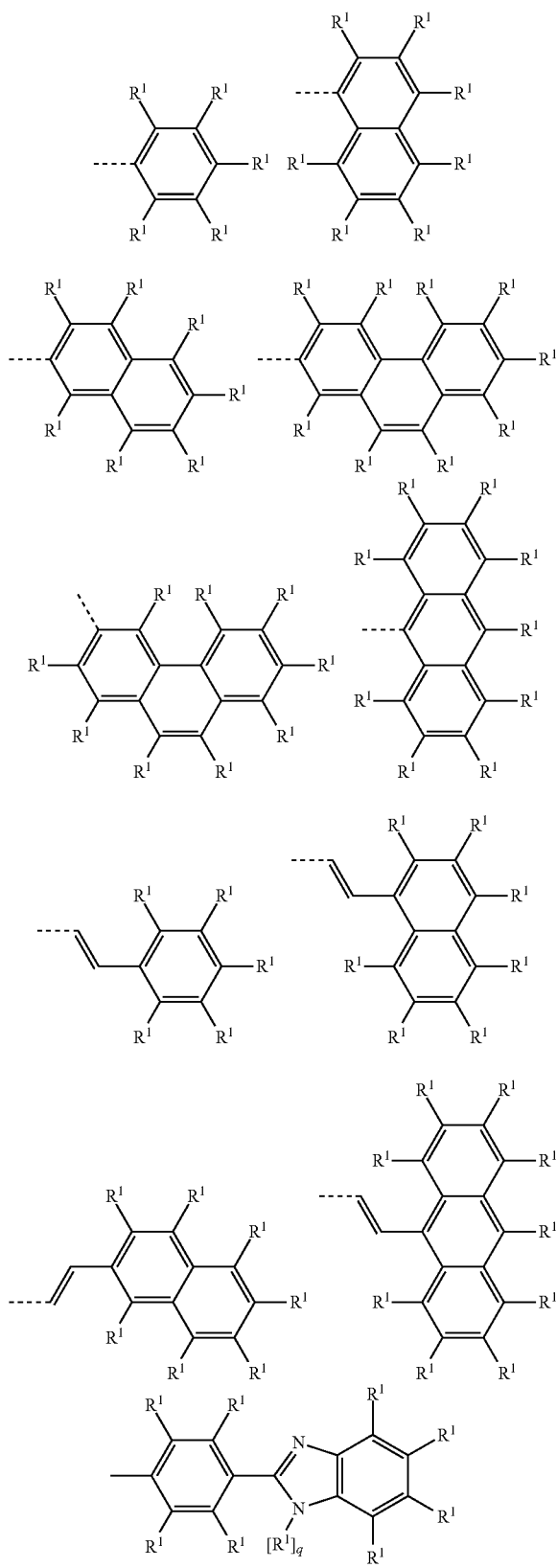

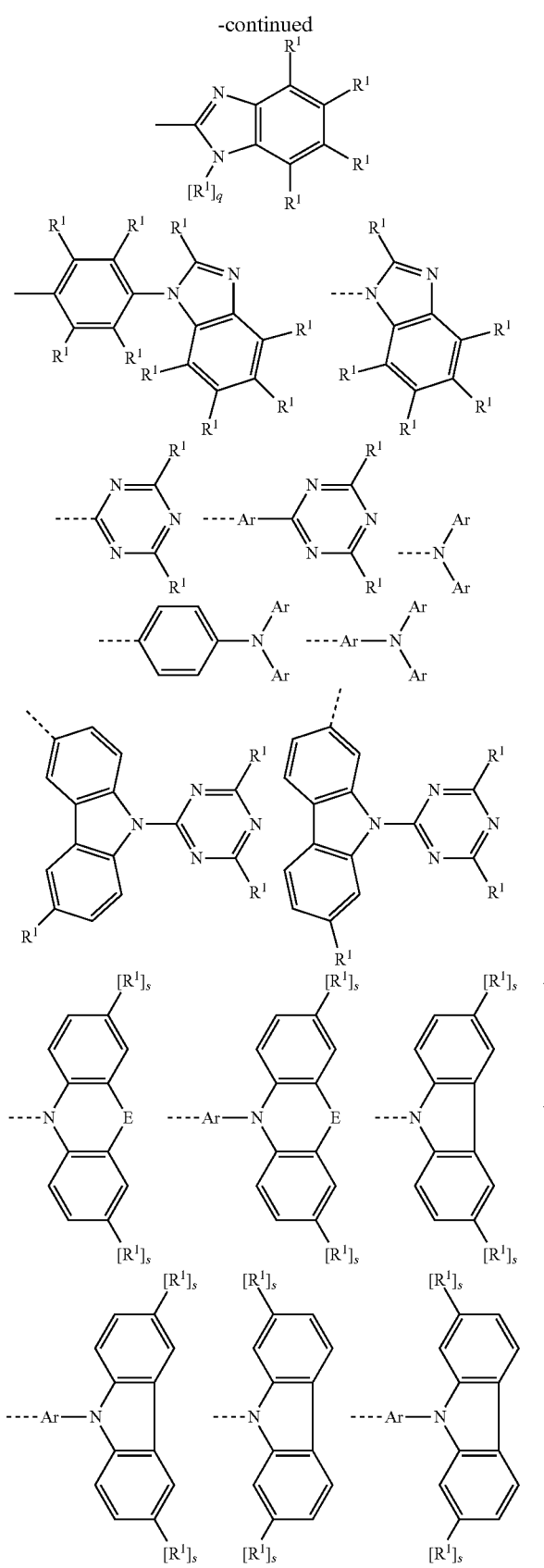

where the dashed line in the groups is intended to indicate that the group is bonded at this position, and where the radicals Ar and $R^1$ are intended to have the same meaning as above, and where s and q are each, independently of one another, 0 or 1, where, for s=0 or q=0, the $R^1$ in question is replaced by an H. E is selected from the group consisting of $C(R^1)_2$, $NR^1$, O, C=O, S, S=O and $S(O)_2$.

In still a further embodiment of the present invention, $R^1$ is preferably selected, identically or differently on each occurrence, from the group consisting of H, D, F, CN, a straight-chain alkyl, alkoxy or thioalkoxy group having 1 to 20 C atoms and a branched or cyclic alkyl, alkoxy or thioalkoxy group having 3 to 20 C atoms; where, in addition, the respective $R^1$ which is located in the vicinal position to the radical R can be a divalent unit, which may be linked to the aromatic or heteroaromatic ring system of the group R.

The divalent aliphatic hydrocarbon unit, which preferably links two aromatic or heteroaromatic hydrocarbon radicals to one another, is preferably a —$CH_2$—$(CH_2)_h$—$CH_2$— group, where h is equal to 0, 1, 2 or 3, and, in the case of the polyvalent, preferably trivalent or tetravalent, unit, is an aliphatic group having 4 to 10 carbon atoms. One or more, preferably one, $CH_2$ groups of these units may be replaced by NH, O or S and one or more, preferably one, CH groups may be replaced by N.

In still a further embodiment of the present invention, Ar is preferably an aromatic or heteroaromatic ring system having 5 to 14 aromatic ring atoms.

In still a further embodiment of the present invention, the compound of the formula I is characterised by the following formula II or III:

formula II formula III where the symbols R and $R^1$ have the same meanings as in the above embodiments. The preferred embodiments mentioned above also apply to the compounds of the formulae II and III.

It is part of the present invention that the said embodiments, or preferred ranges or definitions of the present invention, can be combined with one another as desired.

It is furthermore preferred for the compounds of the general formula I to conform to the following structural formulae:

(1)
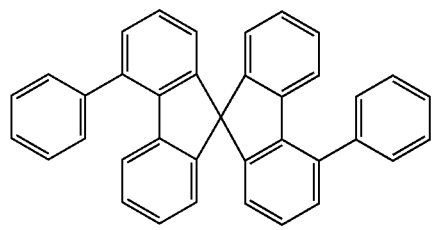
(2)
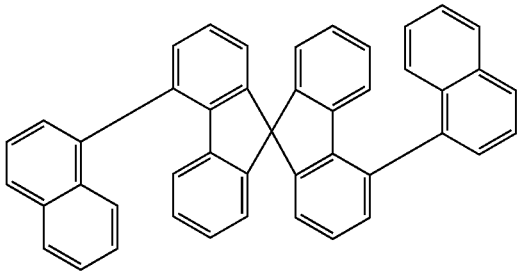
(3)
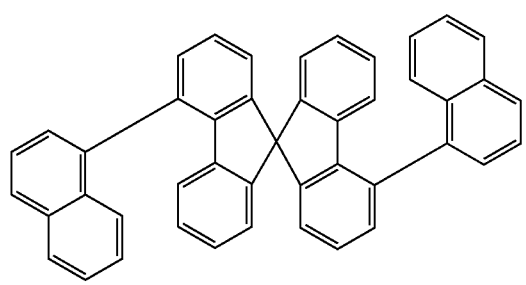
(4)
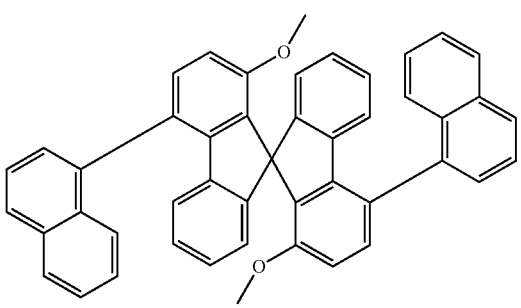
(5)
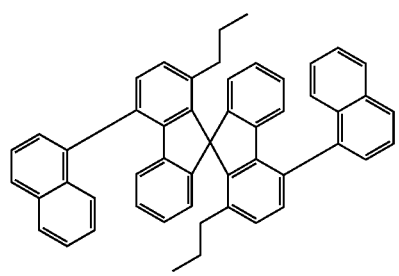
(6)
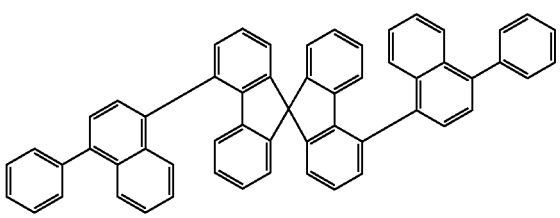
(7)
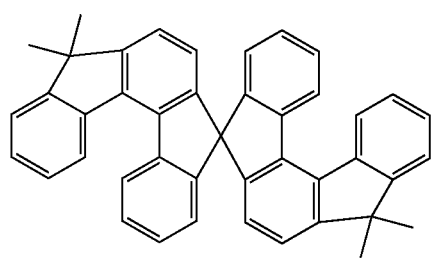
(8)
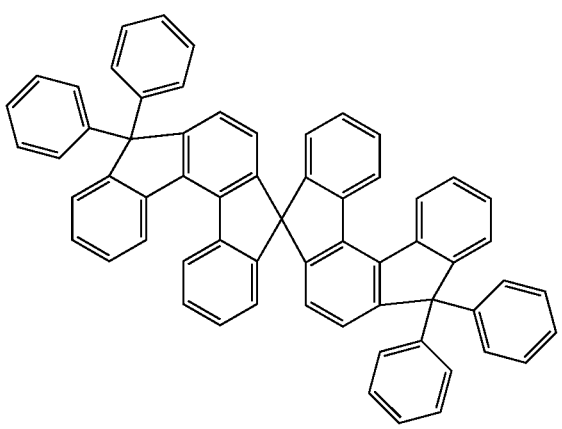
(9)
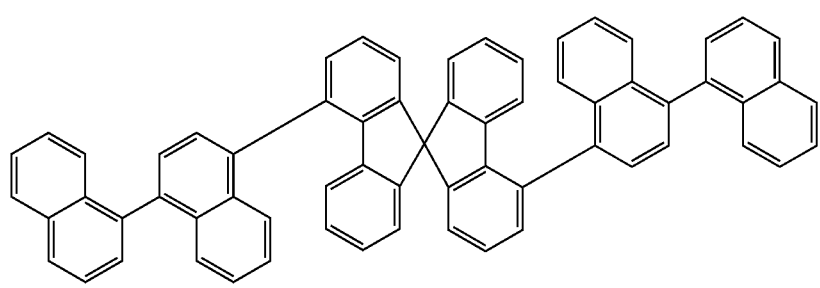

-continued
(10)
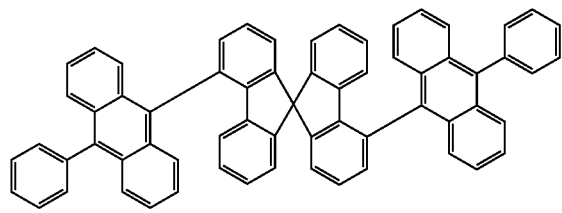
(11)
(12)
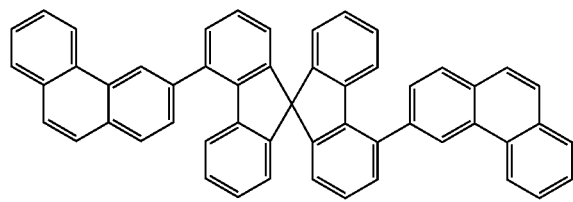
(13)
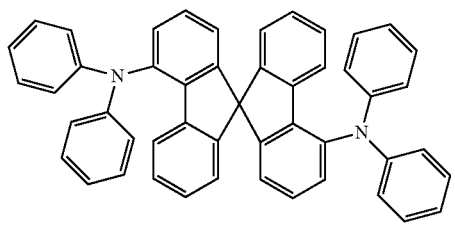
(14)
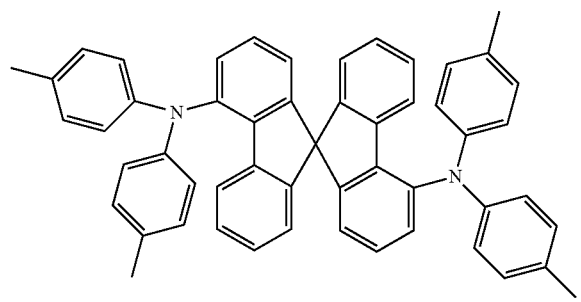
(15)
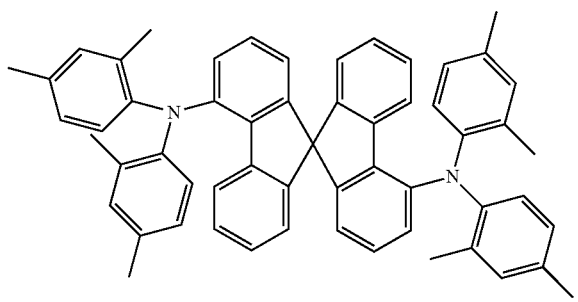
(16)
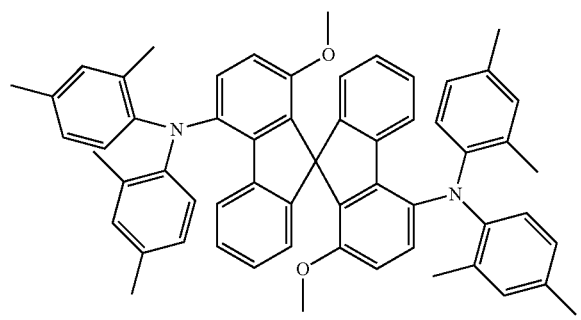
(17)
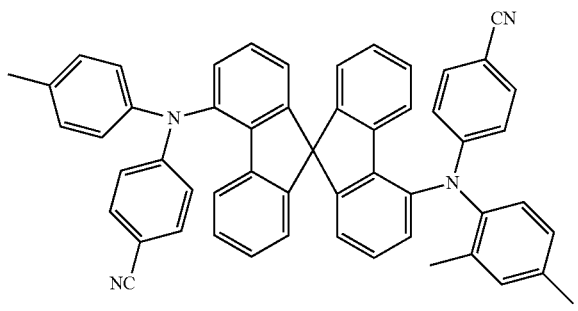
(18)
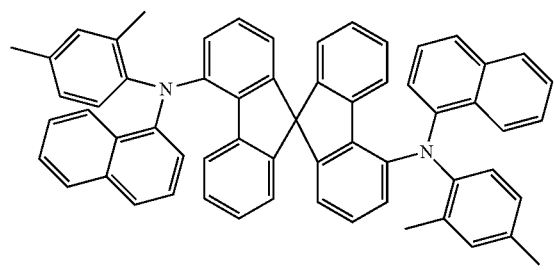
(19)
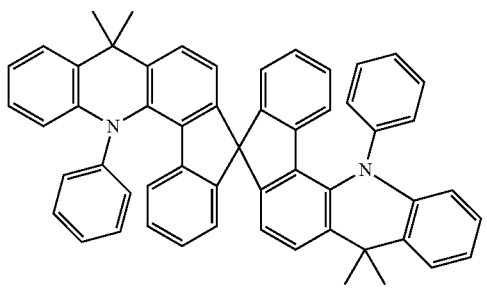

(20)
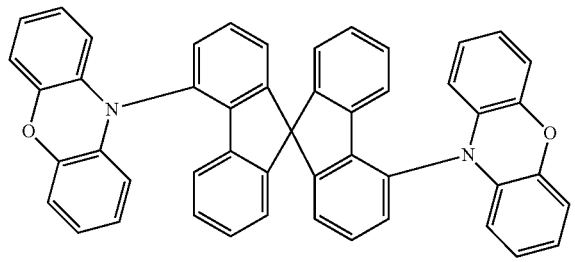
(21)
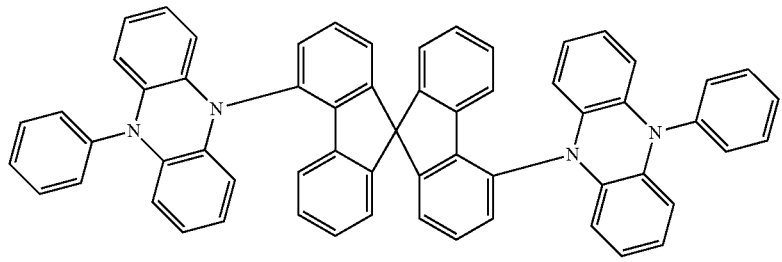
(22)
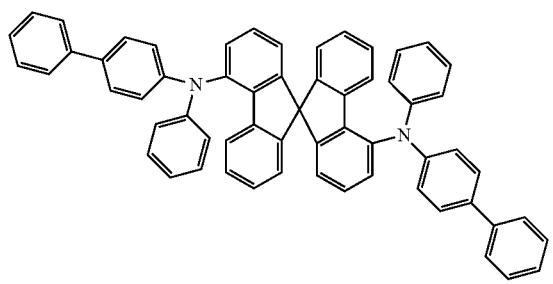
(23)
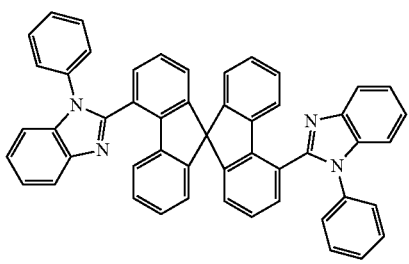
(24)
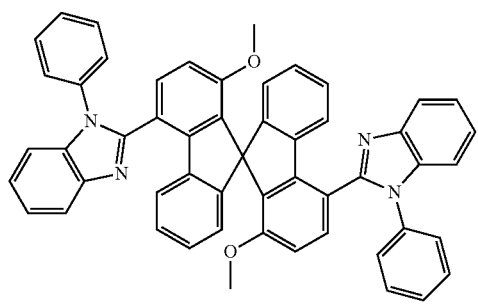
(25)
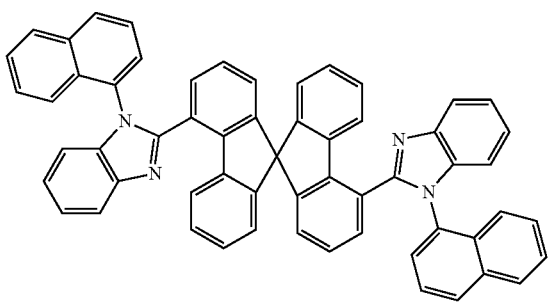
(26)
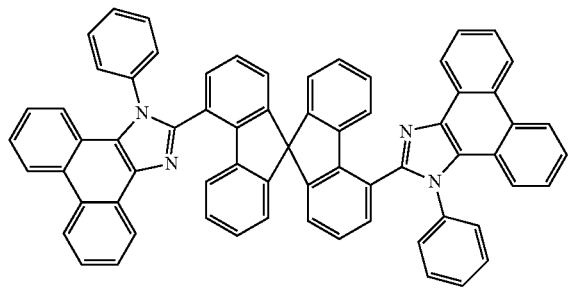
(27)
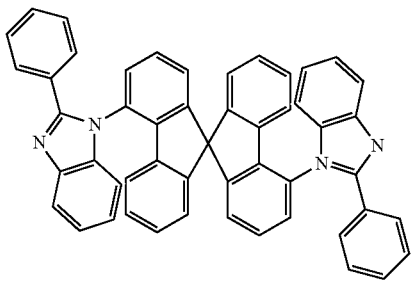

-continued
(28)
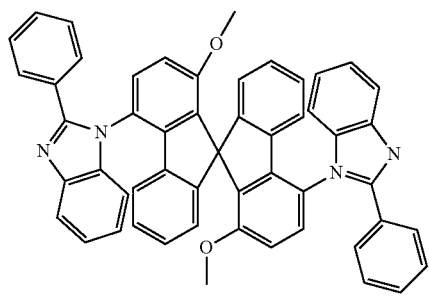
(29)
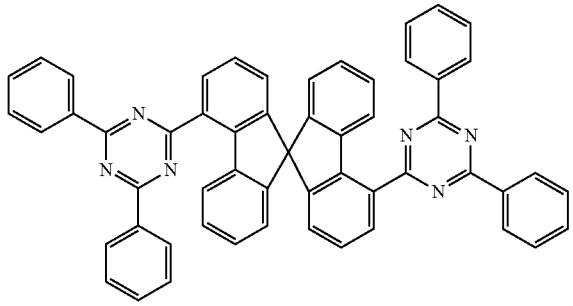
(30) (31)
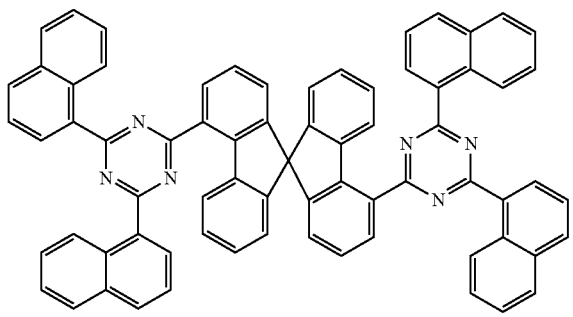
(32) (33)
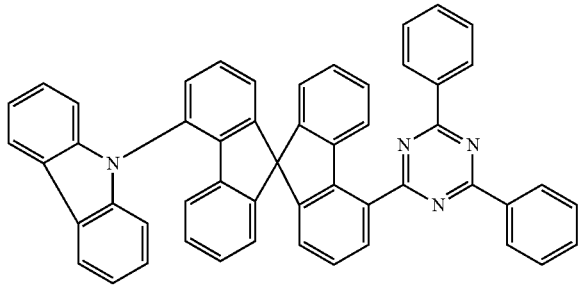
(34) (35)
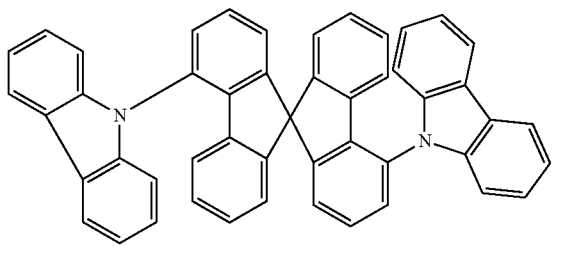
(36)
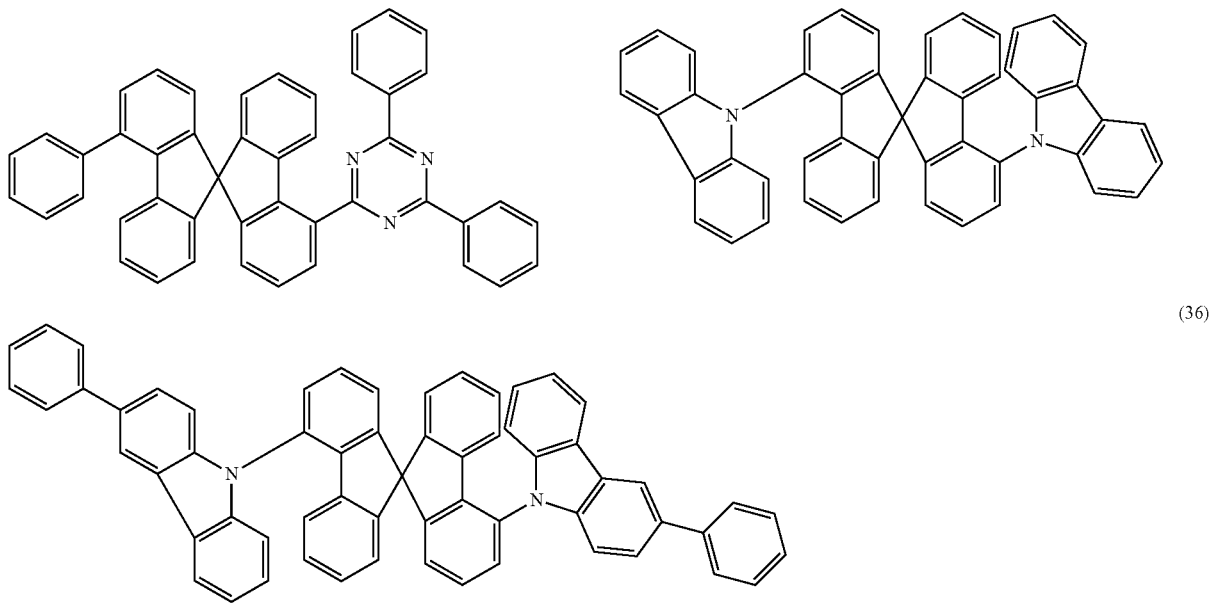

(37)
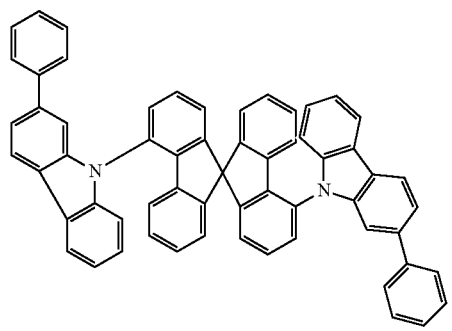
(38)
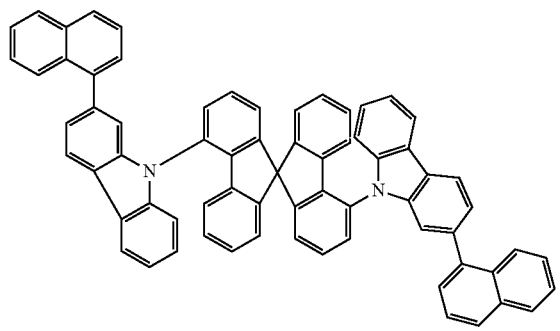
(39)
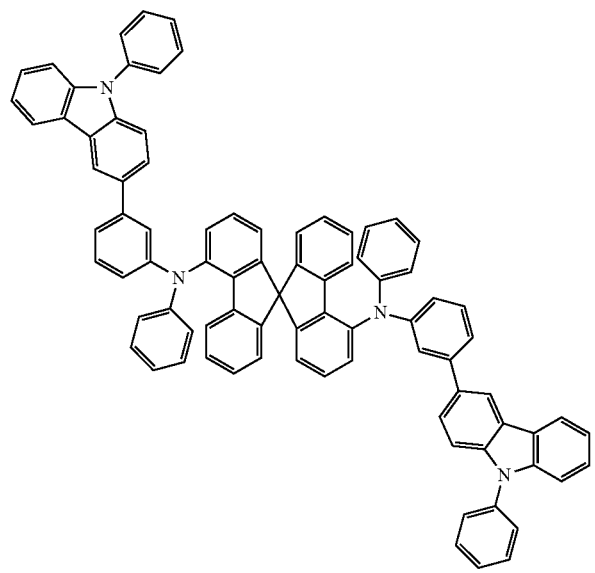
(40)
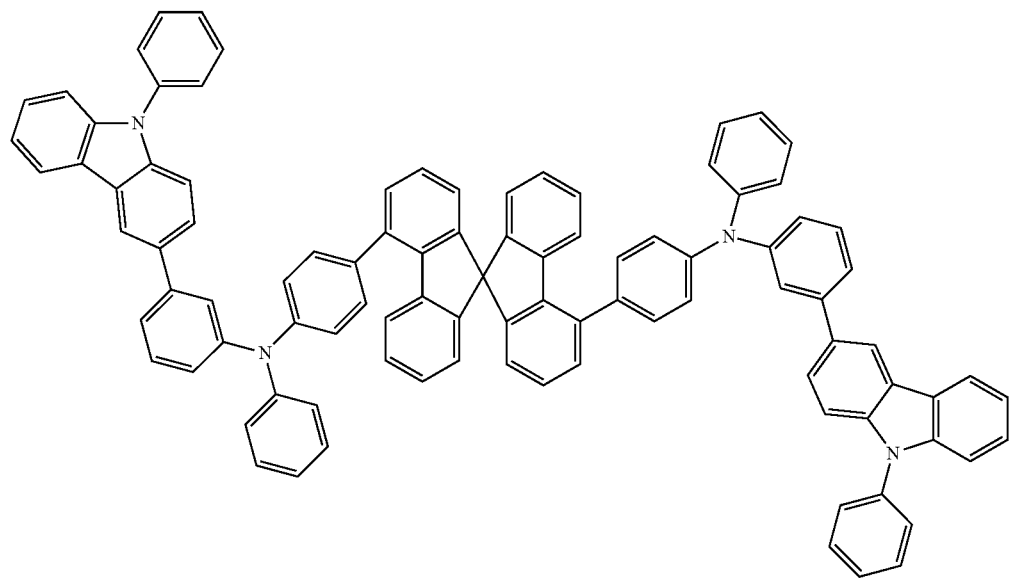

-continued
(41)
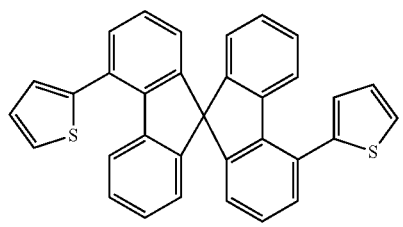
(42)
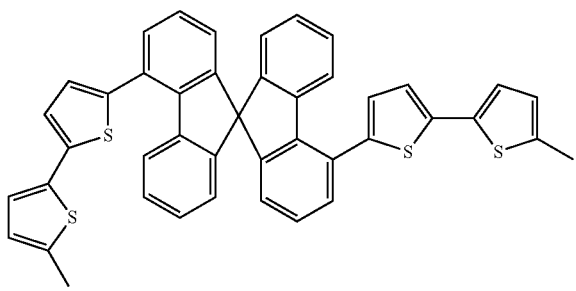
(43)
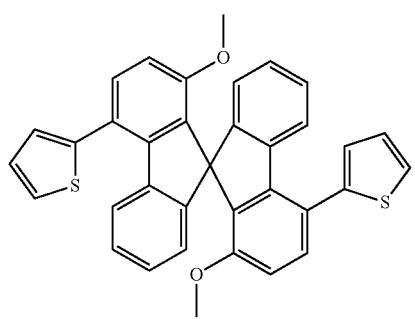
(44)
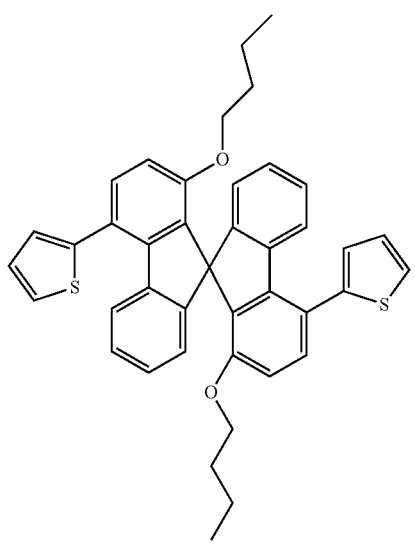
(45)
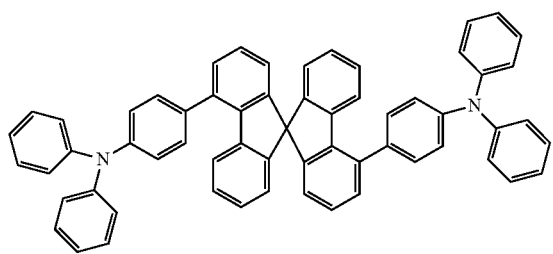
(46)
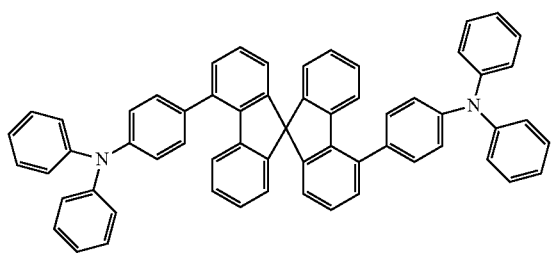

-continued
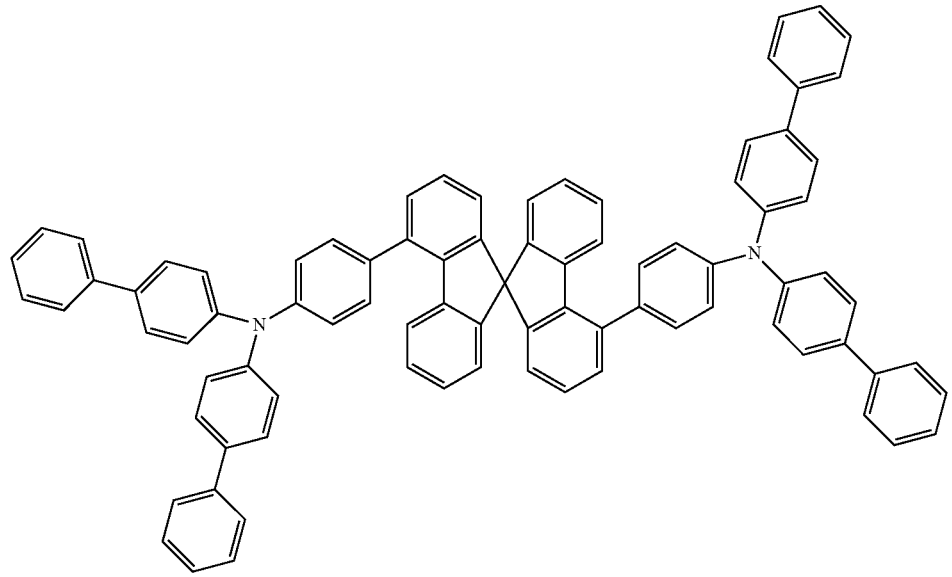
(47)
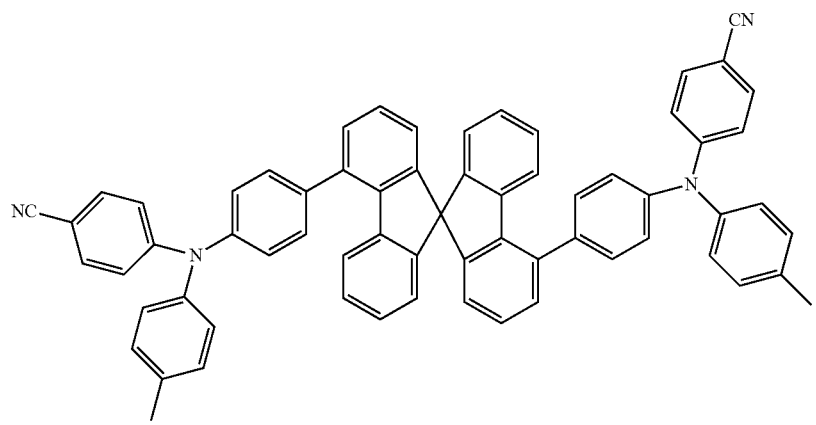
(48)
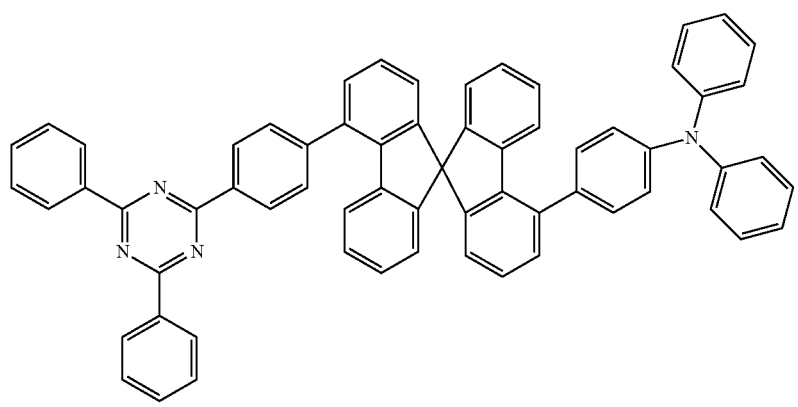
(49)
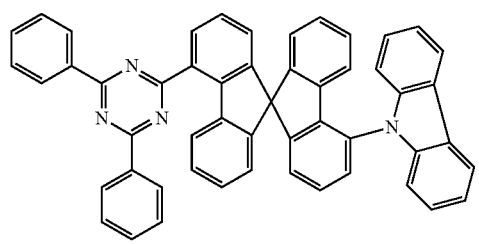
(50)
(51)

-continued

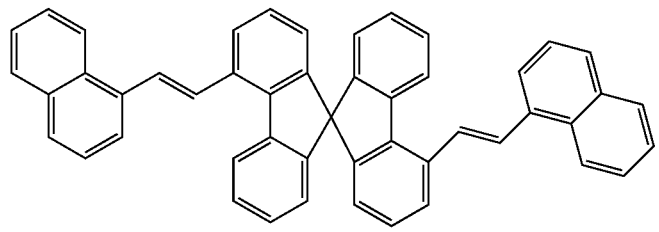

(52)

The compounds according to the invention can be prepared by synthetic steps known to the person skilled in the art. The starting substance used is preferably 4,4'-dibromo-1,1'-dimethoxy-9,9'-spirobifluorene, which can be prepared by the process shown in Scheme 1.

Scheme 1:

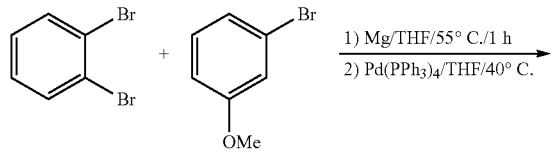

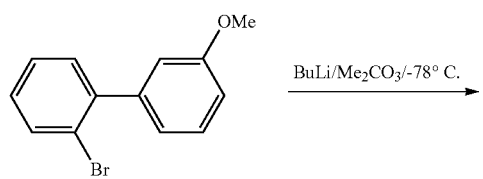

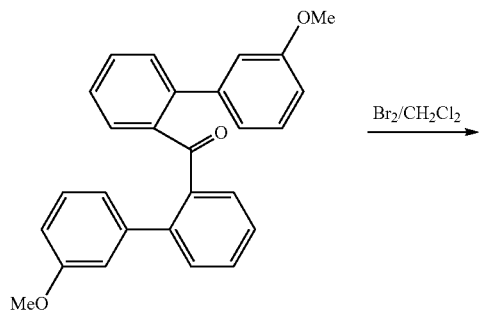

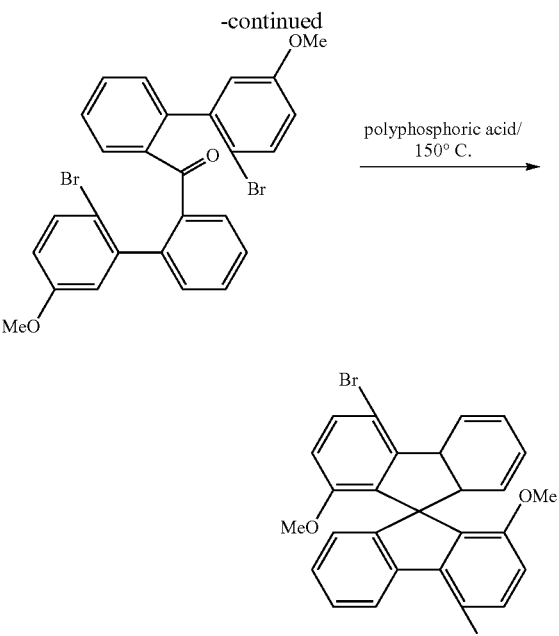

To this end, 1,2-dibromobenzene and 1-methoxy-3-bromobenzene are coupled to one another in a Grignard reaction in a first step to give 2-bromo-5'-methoxybiphenyl. Two of these molecules are subsequently coupled to one another via a CO group in the presence of butyllithium with elimination of the bromine atoms. After subsequent bromination in the respective 2'-position, the cyclisation is carried out in the presence of acid to give 4,4'-dibromo-1,1'-dimethoxy-9,9'-spirobifluorene.

Scheme 2:

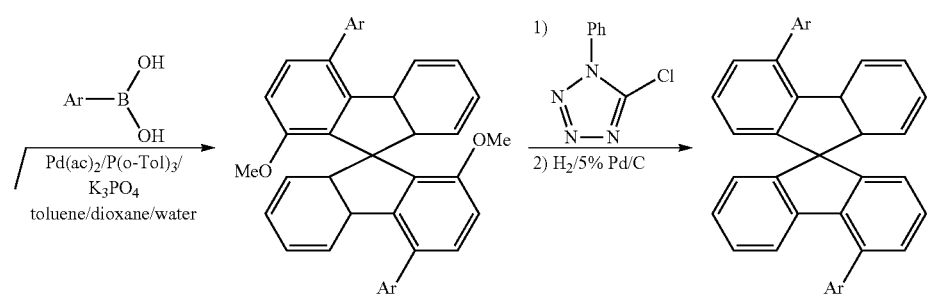

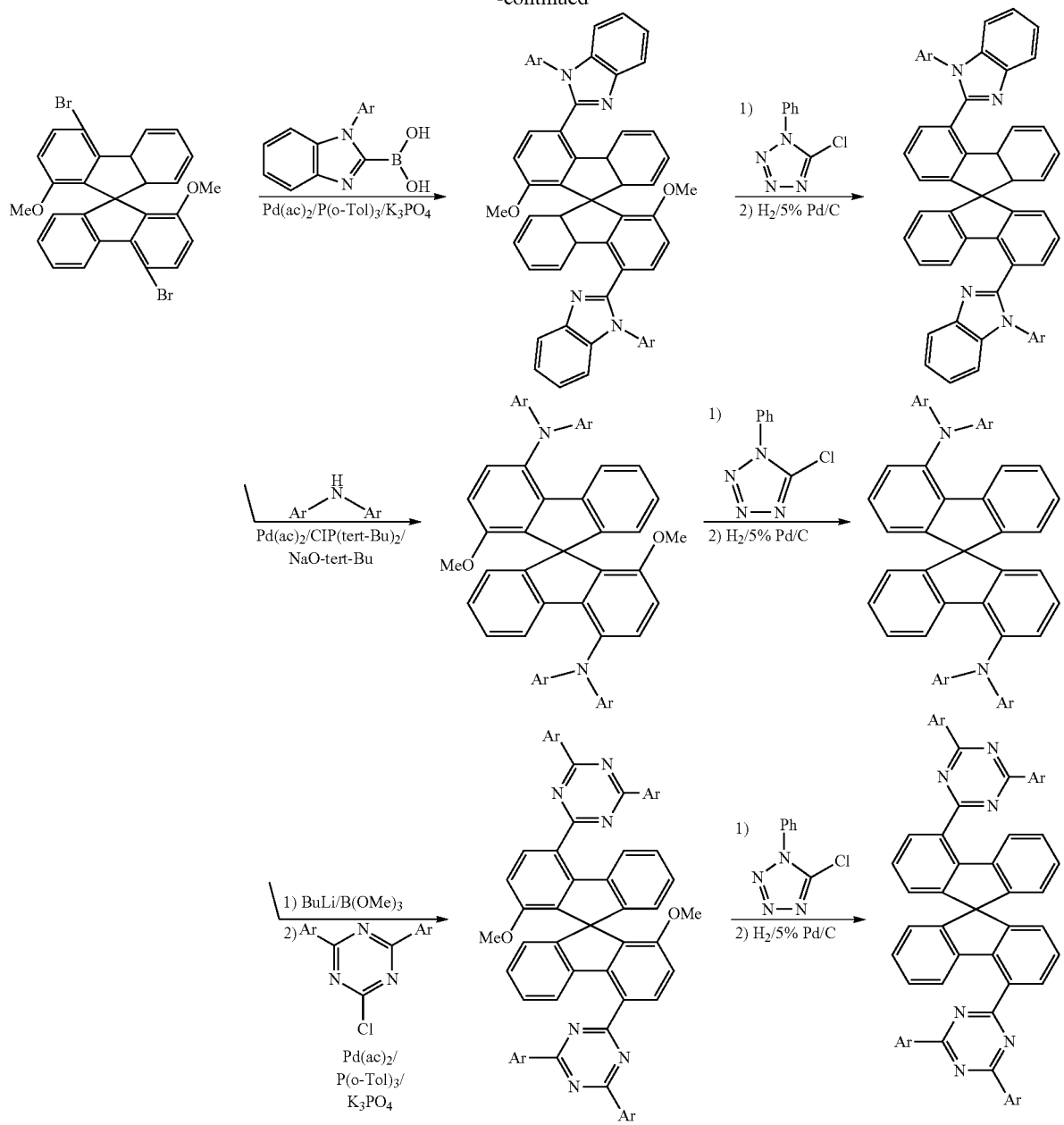

Scheme 2 shows four different possibilities for the preparation of a compound according to the invention from 4,4'-dibromo-1,1'-dimethoxy-9,9'-spirobifluorene. The first two cases involve Suzuki couplings, in which the starting compound is reacted with the corresponding boronic acids. The third reaction is a Hartwig-Buchwald reaction. The final case again involves a Suzuki coupling, in which a boronic acid derivative of the spirobifluorene is reacted with a heteroaromatic chloride. Both types of reaction are known to the person skilled in the art and have been described many times in the literature. A common feature of all schemes is the reductive removal of the methoxy groups, for example by reaction with N-phenyl-5-chlorotetrazole and H$_2$.

The invention furthermore relates to a process for the preparation of a compound of the general formulae I to III, characterised in that a spirobifluorene or a spirobifluorene derivative which is substituted in positions 4 and 4' by a reactive leaving group, in particular chlorine, bromine, iodine, triflate, tosylate, boronic acid or boronic acid ester, is coupled to a functionalised aromatic compound or to a mono- or disubstituted amine, in particular by a Suzuki coupling with palladium catalysis or by a palladium-catalysed Hartwig-Buchwald coupling.

The invention furthermore relates to mixtures comprising at least one compound of the formula I, II or III and at least one further compound. The further compound here can be, for example, an emitting compound, for example a phosphorescent emitter, and/or a host material.

In order to process the compounds according to the invention from solution, solutions and formulations of the compounds are necessary. The present invention therefore furthermore relates to a formulation or solution comprising at least one compound of the formula I, II or III and at least one solvent, preferably an organic solvent.

The invention furthermore relates to the use of the compounds according to the invention defined above in electronic devices.

The invention furthermore relates to an electronic device comprising at least one compound according to the invention, as defined above.

The electronic device is preferably selected from the group consisting of organic electroluminescent devices (OLEDs), organic field-effect transistors (O-FETs), organic thin-film transistors (O-TFTs), organic light-emitting transistors (O-LETS), organic integrated circuits (O-ICs), organic solar cells (O-SCs), organic field-quench devices (O-FQDs), light-emitting electro-chemical cells (LECs), organic photoreceptors or organic laser diodes (O-lasers).

The organic electroluminescent device comprises an anode, a cathode and at least one emitting layer, where at least one layer, which can be a hole-transport or -injection layer, an emitting layer, an electron-transport layer or another layer, comprises at least one compound of the formulae I to III.

Preference is furthermore given to organic electroluminescent devices, characterised in that a plurality of emitting compounds are used in the same layer or in different layers. These compounds particularly preferably have in total a plurality of emission maxima between 380 nm and 750 nm, resulting overall in white emission, i.e. at least one further emitting compound which is able to fluoresce or phosphoresce is used in addition to the compound of the formulae I to III. Particular preference is given to three-layer systems, at least one layer of which comprises a compound of the formulae I to III and where the layers exhibit blue, green and orange or red emission (for the basic structure see, for example, WO 05/011013). Broad-band emitters can likewise be used for white-emitting OLEDs.

Apart from the cathode, anode and emitting layer, the organic electroluminescent device may also comprise further layers. These can be, for example: hole-injection layer, hole-transport layer, electron-blocking layer, exciton-blocking layer, hole-blocking layer, electron-transport layer, electron-injection layer, organic or inorganic p/n junctions and/or charge-generation layer (T. Matsumoto et al., *Multiphoton Organic EL Device Having Charge Generation Layer*, IDMC 2003, Taiwan; Session 21 OLED (5)). However, it should be pointed out at this point that each of these layers does not necessarily have to be present. Alternatively, the host material can also simultaneously serve as electron-transport material in an electron-transport layer. It may likewise be preferred for the organic electroluminescent device not to comprise a separate hole-transport layer and for the emitting layer to be directly adjacent to the hole-injection layer or the anode. It may furthermore be preferred for the compound of the formulae I to III simultaneously to be used as host in the emitting layer and, depending on the substituent, as hole-conducting compound (as pure substance or as mixture) in a hole-transport layer and/or in a hole-injection layer or as electron-conducting compound (as pure substance or as mixture) in an electron-transport layer.

In a preferred embodiment of the invention, the compound of the formulae I to II is employed as hole-transport material and/or as hole-injection material. The emitting layer here can be a fluorescent or phosphorescent layer. This applies not only, but in particular, if R stands for —NAr$_2$ or —Ar—NAr$_2$. The compounds are then preferably employed in a hole-transport layer and/or in a hole-injection layer. A hole-injection layer in the sense of this invention is a is a layer which is directly adjacent to the anode. A hole-transport layer in the sense of this invention is a layer which is located between the hole-injection layer and the emission layer. If the compounds of the formulae I to III are used as hole-transport or hole-injection material, it may be preferred for them to be doped with electron-acceptor compounds, for example with F$_4$-TCNQ (tetrafluorotetracyanoquinodimethane) or with compounds as described in EP 1476881 or EP 1596445.

If the compound of the formulae I to III is employed as hole-transport material in a hole-transport layer, a proportion of 100%, i.e. the use of this compound as pure material, may also be preferred.

In an embodiment of the invention, the compound of the formulae I to III is used in a hole-transport or -injection layer in combination with a layer which comprises a hexaazatriphenylene derivative, in particular hexacyanohexaazatriphenylene (for example in accordance with EP 1175470). Thus, preference is given, for example, to a combination which looks as follows: anode—hexaazatriphenylene derivative—hole-transport layer, where the hole-transport layer comprises one or more compounds of the formulae I to III. It is likewise possible in this structure to use a plurality of successive hole-transport layers, where at least one hole-transport layer comprises at least one compound of the formulae I to III. A further preferred combination looks as follows: anode—hole-transport layer—hexaazatriphenylene derivative—hole-transport layer, where at least one of the two hole-transport layers comprises one or more compounds of the formulae I to III. It is likewise possible in this structure for a plurality of successive hole-transport layers to be used instead of one hole-transport layer, where at least one hole-transport layer comprises at least one compound of the formulae I to III.

It is furthermore preferred for the compounds of the formulae I to III to be employed as electron-transport material and/or hole-blocking material for fluorescent and phosphorescent OLEDs. This is the case, in particular, if R stands for or contains an electron-deficient heteroaromatic radical, for example triazine or benzimidazole, or contains a carbonyl substituent.

In a preferred embodiment of the invention, the compound of the formulae I to III is employed as matrix material for a fluorescent or phosphorescent compound in an emitting layer. The organic electroluminescent device here may comprise one emitting layer or a plurality of emitting layers, where at least one emitting layer comprises at least one compound according to the invention as matrix material.

If the compound of the formulae I to III is employed as matrix material for an emitting compound in an emitting layer, it is preferably employed in combination with one or more phosphorescent materials (triplet emitters). The structure of the compounds according to the invention means that they have a high triplet level and are thus very highly suitable for use in phosphorescent electroluminescent devices. Phosphorescence in the sense of this invention is taken to mean the luminescence from an excited state having a relatively high spin multiplicity, i.e. a spin multiplicity>1, in particular from an excited triplet state. For the purposes of this application, all luminescent complexes containing metals from the second and third transition-metal series, in particular all iridium and platinum complexes, and all luminescent copper complexes, are to be regarded as phosphorescent compounds. The phosphorescent compounds here can be compounds which emit light throughout the visible spectrum, in particular red, orange, yellow, green or blue light.

The mixture of the compound of the formulae I to III or the preferred embodiments and the emitting compound comprises between 99 and 1% by weight, preferably between 98 and 10% by weight, particularly preferably between 97 and 60% by weight, in particular between 95 and 80% by weight, of the compound of the formulae I to III, based on the entire mixture of emitter and matrix material. Correspondingly, the mixture comprises between 1 and 99% by weight, preferably between 2 and 90% by weight, particularly preferably between 3 and 40% by weight, in particular between 5 and 20% by weight, of the emitter, based on the entire mixture of emitter and matrix material.

A further preferred embodiment of the present invention is the use of the compound of the formulae I to III as matrix material for a phosphorescent emitter in combination with a further matrix material. Particularly suitable matrix materials which can be employed in combination with the compounds of the formulae I to III are aromatic ketones, aromatic phosphine oxides or aromatic sulfoxides or sulfones, for example in accordance with WO 04/013080, WO 04/093207, WO 06/005627 or WO 2010/006680, triarylamines, carbazole derivatives, for example CBP (N,N-biscarbazolyl-biphenyl), or the carbazole derivatives disclosed in WO 05/039246, US 2005/0069729, JP 2004/288381, EP 1205527 or WO 08/086, 851, indolocarbazole derivatives, for example in accordance with WO 07/063,754 or WO 08/056,746, azacarbazole derivatives, for example in accordance with EP 1617710, EP 1617711, EP 1731584, JP 2005/347160, bipolar matrix materials, for example in accordance with WO 07/137,725, silanes, for example in accordance with WO 05/111172, azaboroles or boronic esters, for example in accordance with WO 06/117052, triazine derivatives, for example in accordance with WO 2010/015306, WO 07/063,754 or WO 08/056,746, zinc complexes, for example in accordance with EP 652273 or WO 09/062,578, diazasilole or tetraazasilole derivatives, for example in accordance with the unpublished application DE 102008056688.8, diazaphosphole derivatives, for example in accordance with the unpublished application DE 102009022858.9, or indenocarbazole derivatives, for example in accordance with the unpublished applications DE 102009023155.2 and DE 102009031021.5.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 01/41512, WO 02/02714, WO 02/15645, EP 1191613, EP 1191612, EP 1191614, WO 05/033244, WO 05/019373 and US 2005/0258742. Also suitable are, for example, the complexes in accordance with the unpublished applications EP 10006208.2 and DE 102010027317.1. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

In an embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 05/053051. It is furthermore possible to use a metal complex which is identical or similar to the metal complex in the emitting layer as hole-transport or hole-injection material directly adjacent to the emitting layer, as described, for example, in WO 09/030,981.

In still a further embodiment of the invention, the compound of the formulae I to III is employed in a emitting layer, preferably in a mixture with at least one further compound. It is preferred for the compound of the formulae I to III in the mixture to be the emitting compound (the dopant). Preferred host materials are organic compounds whose emission is of shorter wavelength than that of the compound of the formulae I to III or which do not emit.

The proportion of the compound of the formulae I to III in the mixture of the emitting layer is between 0.1 and 99.0% by weight, preferably between 0.5 and 50.0% by weight, particularly preferably between 1.0 and 20.0% by weight, in particular between 1.0 and 10.0% by weight. Correspondingly, the proportion of the host material in the layer is between 1.0 and 99.9% by weight, preferably between 50.0 and 99.5% by weight, particularly preferably between 80.0 and 99.0% by weight, in particular between 90.0 and 99.0% by weight.

Suitable host materials are various classes of substance. Preferred host materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 or WO 05/084082), the atropisomers (for example in accordance with EP 1655359), the boronic acid derivatives (for example in accordance with WO 06/117052), the benzanthracene derivatives (for example in accordance with WO 08/145,239) or the benzphenanthrene derivatives (for example in accordance with WO 09/069,566 or in accordance with the unpublished application DE 102009005746.3). Particularly preferred host materials are selected from the classes of the oligoarylenes, comprising naphthalene, anthracene, benzanthracene and/or pyrene, or atropisomers of these compounds, the oligoarylenevinylenes, the ketones, the phosphine oxides and the sulfoxides. Very particularly preferred host materials are selected from the classes of the oligoarylenes, comprising naphthalene, anthracene, benzanthracene, benzphenanthrene and/or pyrene, or atropisomers of these compounds.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). In the case of multilayered structures, further metals which have a relatively high work function, such as, for example, Ag, can also be used in addition to the said metals, in which case combinations of the metals, such as, for example, Mg/Ag, Ca/Ag or Ba/Ag, are generally used. Preference is likewise given to metal alloys, in particular alloys comprising an alkali metal or alkaline-earth metal and silver, particularly preferably an alloy of Mg and Ag. It may also be preferred to introduce a thin interlayer of a material having a high dielectric constant between a metallic cathode and the organic semiconductor.

Suitable for this purpose are, for example, alkali-metal or alkaline-earth metal fluorides, but also the corresponding oxides or carbonates (for example LiF, $Li_2O$, CsF, $Cs_2CO_3$, $BaF_2$, MgO, NaF, etc.) as are organic complexes of these metals, such as, for example, lithium quinolinate (Liq). The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to enable either the irradiation of the organic material (O-SC) or the coupling-out of light (OLEDs/PLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is structured correspondingly (depending on the application), provided with contacts and finally hermetically sealed, since the lifetime of devices of this type is drastically shortened in the presence of water and/or air.

Preference is furthermore given to an organic electroluminescent device, characterised in that one or more layers are applied by means of a sublimation process, in which the materials are applied by vapour deposition in vacuum sublimation units at an initial pressure of less than $10^{-5}$ mbar, preferably less than $10^{-6}$ mbar. However, it should be noted that the initial pressure may also be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), inkjet printing or nozzle printing. Soluble compounds of the formulae I to III are required for this purpose. High solubility can be achieved through suitable substitution of the compounds.

On use in organic electroluminescent devices, the compounds according to the invention have the following surprising advantages over the prior art:

1. The quantum efficiency of corresponding devices becomes higher compared with systems in accordance with the prior art in which comparable substituents are bonded in the 2,2'-position on the spirobifluorene. The reason for this is possibly that quenching effects are reduced due to the absence of a para-linked biphenyl bridge and the greater geometrical disorder in the film.
2. The stability of corresponding devices becomes higher compared with systems in accordance with the prior art, which is evident, in particular, from a significantly longer lifetime, in particular on use of thick layers.
3. On use of the compounds according to the invention as hole-transport material in a hole-transport and/or hole-injection layer, it is evident that the voltage is less dependent on the layer thickness of the corresponding hole-transport or hole-injection layer. By contrast, a greater increase in voltage is obtained with materials in accordance with the prior art in the case of relatively thick layer thicknesses of the hole-transport or hole-injection layers, which in turn results in lower power efficiency of the OLED.
4. In particular, however, the crystallinity of the compounds according to the invention is improved. Whereas the compounds in accordance with the prior art in some cases crystallise on the vapour-deposition source during vapour deposition and thus result in blockage of the source on extended vapour deposition, as occurs in industrial mass production, this phenomenon is not observed at all or only to a minimal extent in the case of the compounds according to the invention. The compounds according to the invention are therefore more suitable for use in mass production than the compounds in accordance with the prior art.
5. The high triplet level makes the compounds according to the invention also suitable for use in blue- and green-phosphorescent electro-luminescent devices, whereas corresponding 2,2'-substituted spirobifluorene derivatives are less suitable for this purpose.

The present application text and also the examples below are directed to the use of the compounds according to the invention in relation to OLEDs and the corresponding displays. In spite of this restriction of the description, it is possible for the person skilled in the art, without further inventive step, also to employ the compounds according to the invention for further uses in other electronic devices.

The invention will now be explained in greater detail by the following examples, without wishing to restrict it thereby. The person skilled in the art will be able to carry out the invention throughout the range disclosed on the basis of the descriptions and prepare further compounds according to the invention without inventive step and use them in electronic devices or use the process according to the invention.

EXAMPLES

The following syntheses are, unless indicated otherwise, carried out under a protective-gas atmosphere in dried solvents. The 4,4'-dibromo-1,1'-dimethoxy-9,9'-spirobifluorene used as starting material can be synthesised in accordance with X. Cheng et al., Organic Letters 2004, 6(14), 2381-2383.

Example 1

Synthesis of 4,4'-bis(naphth-1-yl)-1,1'-dimethoxy-9,9'-spirobifluorene

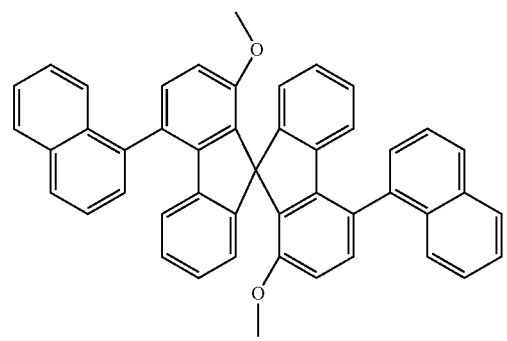 [SMILES: COc1ccc(-c2cccc3ccccc23)c2c1C1(c3ccccc3-2)c2ccccc2-c2c(-c3cccc4ccccc34)ccc(OC)c21]

25.5 g (120 mmol) of tripotassium phosphate in a mixture of 300 ml of toluene, 100 ml of dioxane and 400 ml of water, 913 mg (3 mmol) of tri-o-tolylphosphine and then 112 mg (0.5 mmol) of palladium(II) acetate are added to a well-stirred suspension of 26.7 g (50 mmol) of 4,4'-dibromo-1,1'-dimethoxy-9,9'-spirobifluorene and 22.4 g (130 mmol) of 1-naphthylboronic acid, and the mixture is subsequently heated under reflux for 16 h. After cooling, the precipitated solid is filtered off with suction, washed three times with 50 ml of toluene, three times with 50 ml of ethanol:water (1:1, v:v) and three times with 100 ml of ethanol and subsequently recrystallised three times from DMF (about 10 ml/g). Yield: 20 g (31 mmol), 65.0%, purity: 99.9% (HPLC).

Example 2

Synthesis of 4,4'-bis(naphth-1-yl)-9,9'-spirobifluorene

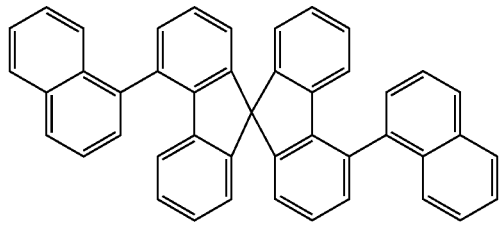 [SMILES: c1ccc2c(c1)-c1c(-c3cccc4ccccc34)cccc1C21c2ccccc2-c2c(-c3cccc4ccccc34)cccc21]

A well-stirred suspension of 31.5 g (50 mmol) of 4,4'-bis(naphth-1-yl)-1,1'-dimethoxy-9,9'-spirobifluorene, 18.1 g (100 mmol) of 1-phenyl-5-chloro-tetrazole and 27.6 g (200 mmol) of K$_2$CO$_3$ is heated under reflux for 18 h in 250 ml of acetone. After cooling, the precipitated solid is filtered off with suction and dried. The solid is dissolved in 200 ml of toluene, 6 g of 5% Pd/C are added, and the mixture is stirred at 40° C. for 8 h under a hydrogen atmosphere. After removal of the solvent, the residue is washed three times with 50 ml of ethanol:water (1:1, v:v) and three times with 100 ml of ethanol and subsequently recrystallised three times from DMF (about 10 ml/g). Yield: 18.7 g (33 mmol), 69.0%, purity: 99.9% (HPLC).

Example 3

Synthesis of 4,4'-bis(diphenylamino)-1,1'-dimethoxy-9,9'-spirobifluorene

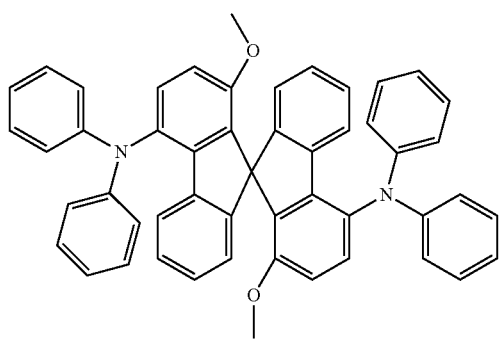 [SMILES: COc1ccc(N(c2ccccc2)c2ccccc2)c2c1C1(c3ccccc3-2)c2ccccc2-c2c(N(c3ccccc3)c3ccccc3)ccc(OC)c21]

190 μl (1 mmol) of di-tert-butylphosphine chloride and then 112 mg (0.5 mmol) of palladium(II) acetate are added to a suspension of 19.7 g (37 mmol) of 4,4'-dibromo-1,1'-dimethoxy-9,9'-spirobifluorene, 10.2 g (60 mmol) of diphenylamine and 7.7 g (80 mmol) of sodium tert-butoxide in 500 ml of toluene, and the mixture is subsequently heated under reflux for 5 h. After cooling to 60° C., 500 ml of water are added, the organic phase is separated off, filtered through silica gel and evaporated virtually to dryness in vacuo at 80° C., and 300 ml of ethanol are then added. After cooling, the solid is filtered off with suction. Recrystallisation five times from dioxane (about 8 ml/g). Yield: 18.8 g (26.5 mmol), 72%, purity 87% (HPLC).

Example 4

Synthesis of 4,4'-bis(diphenylamino)-9,9'-spirobifluorene

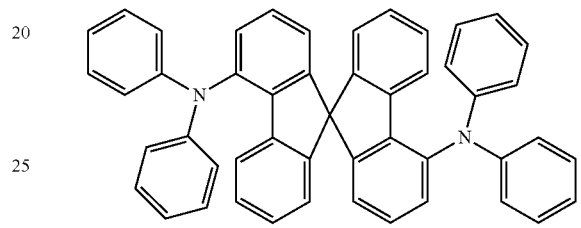

A well-stirred suspension of 35.5 g (50 mmol) of 4,4'-bis(diphenylamino)-1,1'-dimethoxy-9,9'-spirobifluorene, 18.1 g (100 mmol) of 1-phenyl-5-chlorotetrazole and 27.6 g (200 mmol) of K$_2$CO$_3$ is heated under reflux for 18 h in 250 ml of acetone. After cooling, the precipitated solid is filtered off with suction and dried. The solid is dissolved in 200 ml of toluene, 6 g of Pd/C (5%) are added, and the mixture is stirred at 40° C. for 8 h under a hydrogen atmosphere. After removal of the solvent, the residue is washed three times with 50 ml of ethanol:water (1:1, v:v) and three times with 100 ml of ethanol and subsequently recrystallised three times from DMF (about 10 ml/g). Yield: 21.1 g (32.43 mmol), 65.0%, purity: 99.9% (HPLC).

Example 5

Synthesis of 1,1'-dimethoxy-9,9'-spirobifluorene-4,4'-boronic acid

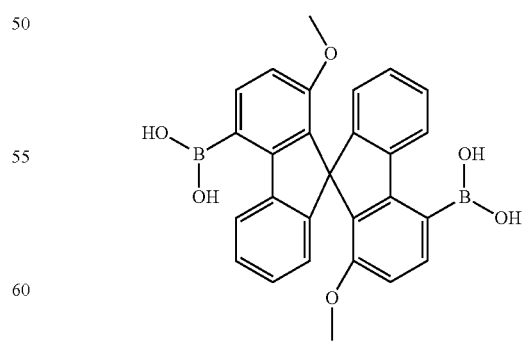

73.7 ml (184 mmol) of n-butyllithium (2.5 M in hexane) are added dropwise to a solution, cooled to −78° C., of 48 g (90 mmol) of 4,4'-dibromo-1,1'-dimethoxy-9,9'-spirobifluorene in 950 ml of diethyl ether. The reaction mixture is stirred at −78° C. for 30 min. The mixture is allowed to come to room temperature and is re-cooled to −78° C., and a mixture of 26.4 ml (234 mmol) of trimethyl borate in 50 ml of diethyl ether is then added rapidly. After warming to −10° C., the mixture is hydrolysed using 90 ml of 2N hydrochloric acid. The organic phase is separated off, washed with water, dried over sodium sulfate and evaporated to dryness. The residue is taken up in 200 ml of n-heptane, and the colourless solid is filtered off with suction, washed with n-heptane and dried in vacuo. Yield: 40.5 g (870 mmol), 97% of theory; purity: 97% according to $^1$H-NMR.

Example 6

Synthesis of 4,4'-bis(4,6-diphenyl-1,3,5-triazin-2-yl)-1,1'-dimethoxy-9,9'-spirobifluorene

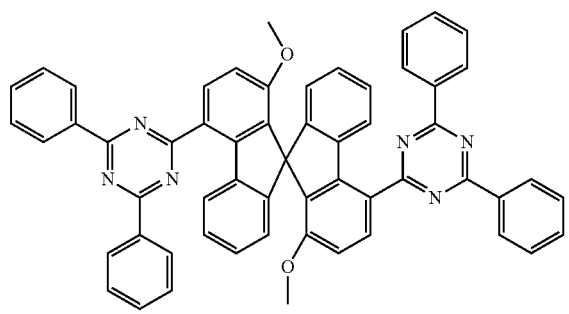 [SMILES: COc1ccc(-c2nc(-c3ccccc3)nc(-c3ccccc3)n2)c2c1C1(c3ccccc3-2)c2ccccc2-c2c(-c3nc(-c4ccccc4)nc(-c4ccccc4)n3)ccc(OC)c21]

23.2 g (50 mmol) of 1,1'-dimethoxy-9,9'-spirobifluorene-4,4'-boronic acid, 29.5 g (110 mmol) of 2-chloro-4,6-diphenyl-1,3,5-triazine and 44.6 g (210 mmol) of tripotassium phosphate are suspended in 500 ml of toluene, 500 ml of dioxane and 500 ml of water. 913 mg (3 mmol) of tri-o-tolylphosphine and then 112 mg (0.5 mmol) of palladium(II) acetate are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from dichloro-methane/isopropanol and finally sublimed in a high vacuum (p=5×10$^{-5}$ mbar, T=385° C.). The yield is 36.4 g (43 mmol), corresponding to 87.5% of theory. Purity: 98% according to $^1$H-NMR.

Example 7

Synthesis of 4,4'-bis(4,6-diphenyl-1,3,5-triazin-2-yl)-9,9'-spirobifluorene

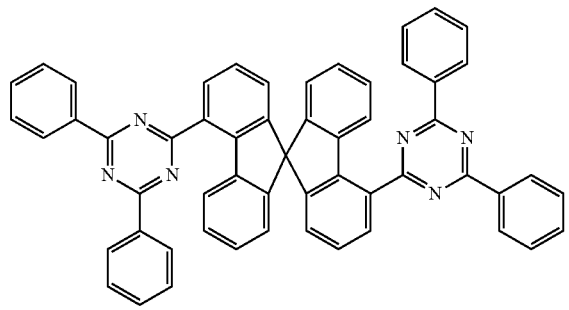 [SMILES: c1ccc(-c2nc(-c3ccccc3)nc(-c3cccc4c3-c3ccccc3C43c4ccccc4-c4c(-c5nc(-c6ccccc6)nc(-c6ccccc6)n5)cccc43)n2)cc1]

A well-stirred suspension of 41.9 g (50 mmol) of 4,4'-bis(4,6-diphenyl-1,3,5-triazin-2-yl)-1,1'-dimethoxy-9,9'-spirobifluorene, 18.1 g (100 mmol) of 1-phenyl-5-chlorotetrazole and 27.6 g (200 mmol) of K$_2$CO$_3$ is heated under reflux for 18 h in 250 ml of acetone. After cooling, the precipitated solid is filtered off with suction and dried. The solid is dissolved in 200 ml of toluene, 6 g of Pd/C (5%) are added, and the mixture is stirred at 40° C. for 8 h under a hydrogen atmosphere. After removal of the solvent, the residue is washed three times with 50 ml of ethanol:water (1:1, v:v) and three times with 100 ml of ethanol and subsequently recrystallised three times from DMF (about 10 ml/g). Yield: 25.6 g (32.96 mmol), 66.0%, purity: 99.9% (HPLC).

Use Examples

Examples 8 to 12 and Comparative Examples 1 to 5

In order to be able to demonstrate the advantages of 4,4'-substituted spiro materials, OLED devices are produced from solution for the present invention. Firstly here, it is relatively simple to mix materials, and secondly the layer thicknesses of the emitting layer (EML) are generally so much greater than in the case of other production processes that transport materials must also be present in the EML (EML from solution typically 60-80 nm, vapour-deposited: 20-40 nm). However, the concentrations of these transport materials generally vary in the region of ~20% by weight, meaning that complete quenching of the emission cannot be expected. However, comparison of 2,2'-substituted spirobifluorenes with 4,4'-substituted spirobifluorenes enables a systematic improvement in the efficiency to be demonstrated in the case of the 4,4'-linked materials.

The production of solution-processed OLEDs is also based on polymeric organic light-emitting diodes (PLEDs) for small molecules. This has already been described many times in the literature (for example in WO 04/037887). A typical device has the structure depicted in FIG. 1, where it should be noted that the central layer 3 is optional. The numbers in FIG. 1 have the following meanings:
1: ITO (indium tin oxide);
2: PEDOT buffer layer, about 80 nm;
3: Interlayer, about 20 nm;
4: EML, about 80 nm;
5: Ba/Al cathode; 3 nm/150 nm.

Figure 2:
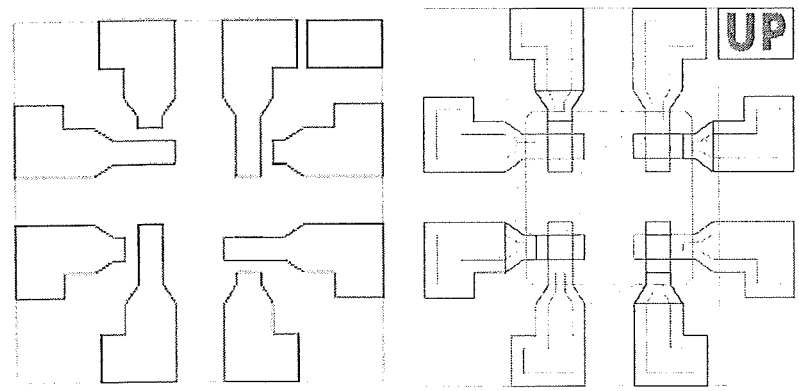

For the production of solution-processed OLEDs, the following procedure is followed:

Especially manufactured substrates from Technoprint are used in a layout designed specifically for the construction of test devices (FIG. 2, left-hand diagram: ITO structure applied to the glass support, right-hand diagram: complete electronic structure with ITO, vapour-deposited cathode and optional metallisation of the supply lines). The ITO structure (indium tin oxide, a transparent, conductive anode) is applied to soda-lime glass by sputtering in a pattern such that 4 pixels of 2×2 mm arise with the cathode vapour-deposited at the end of the production process.

The substrates are cleaned with deionised water and a detergent (Deconex 15 PF) in a clean room and then activated by UV/ozone plasma treatment (15 min UV Ozone Photoreactor from UVP). An 80 nm layer of PEDOT (PEDOT is a polythiophene derivative (Baytron P VAI 4083sp.) from H. C. Starck, Goslar, which is supplied as an aqueous dispersion) is then applied by spin coating, likewise in a clean room. The spin rate required depends on the degree of dilution and the specific spin-coater geometry (typical for 80 nm: 4500 rpm). In order to remove residual water from the layer, the substrates are heated on a hotplate at 180° C. for 10 minutes. Then, firstly 20 nm of an interlayer (typically a hole-dominated polymer, here HIL-012 from Merck) and then 80 nm of the active layer are applied from toluene solutions (concentration of interlayer 5 g/l, solids concentration for small molecules typically between 12 and 30 mg/ml), if necessary under an inert-gas atmosphere (nitrogen or argon). The two layers are dried by heating at 180° C. for at least 10 minutes. The Ba/Al cathode is then vapour-deposited in the pattern indicated through a vapour-deposition mask (high-purity metals from Aldrich, particularly barium 99.99% (Order No. 474711); vapour-deposition units from Lesker or others, typical vacuum level $5 \times 10^{-6}$ mbar). In order to protect the cathode, in particular, against air and atmospheric moisture, the device is finally encapsulated and then characterised.

Figure 3:
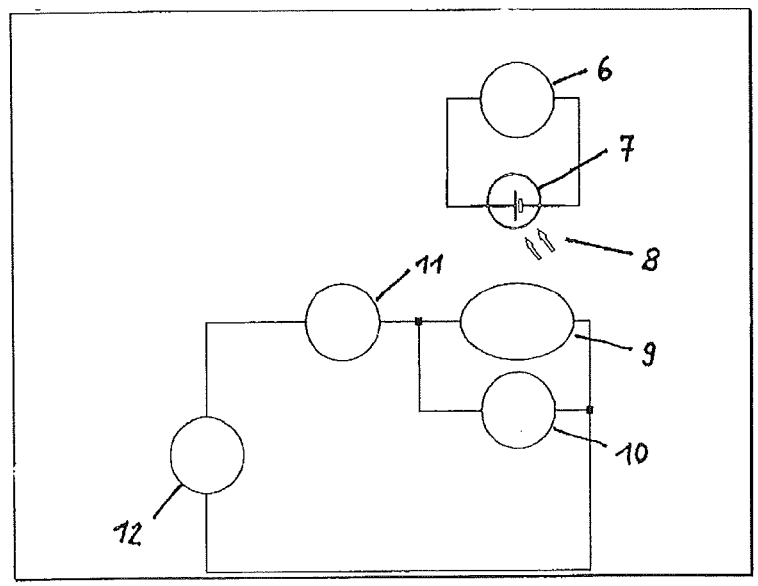

To this end, the devices are clamped into holders specifically manufactured for the substrate size and provided with spring contacts. A photodiode with eye response filter can be placed directly on the measurement holder in order to exclude influences from extraneous light. The typical measurement set-up is depicted in FIG. 3. The numbers in FIG. 3 have the following meanings:

6: electrometer (Keithley 617);
7: measuring instrument for measurement of the light intensity (UDT 265 brightness sensor);
8: the arrows indicate the light intensity to be measured (hv);
9: device for which the light intensity is measured;
10: voltmeter (Keithley 199 DMM);
11: ammeter (Keithley 199 DMM);
12: voltage source (Keithley 230).

The voltages are typically increased from 0 to max. 20 V in 0.2 V steps and reduced again. For each measurement point, the current through the devices and the photocurrent obtained are measured by the photodiode. In this way, the IUL data of the test devices are obtained. The most important parameter here is the maximum efficiency measured ("max. eff." in cd/A).

In order, in addition, to know the colour and the precise electroluminescence spectrum of the test devices, the voltage required for 100 cd/m$^2$ is applied again after the first measurement, and the photodiode is replaced by a spectrum measurement head. This is connected to a spectrometer (Ocean Optics) by an optical fibre. The colour coordinates (CIE: Commission Internationale de l'éclairage, standard observer from 1931) can be derived from the measured spectrum.

Of particular importance for the usability of the materials is the lifetime of the devices. This is measured in a measurement set-up which is very similar to the first evaluation in such a way that an initial luminous density is set (for example 1000 cd/m$^2$). The current required for this luminous density is kept constant, while the voltage typically increases and the luminous density decreases. The lifetime is reached when the initial luminous density has dropped to 50% of the initial value.

The structures of the materials used are depicted below for clarity:

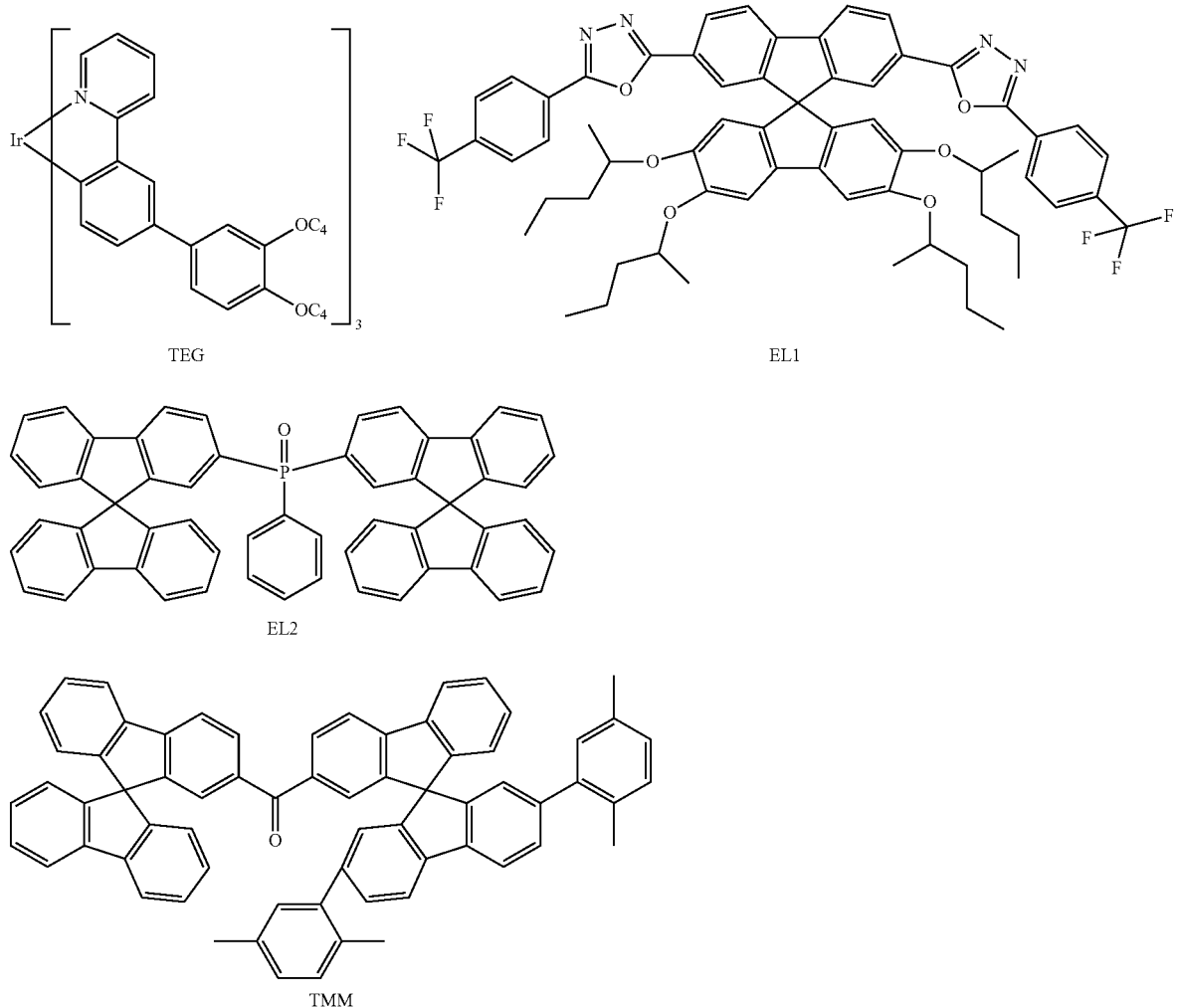

In order to explain the invention, firstly green triplet devices without an interlayer are produced in Examples 8 and 9 and Comparative Examples 1 and 2. The composition of the layer consists in each case of 8% of triplet emitter (TEG, from Merck) in a matrix consisting of 30% of polystyrene as binder (GPC Standard from Alfa Aesar, 200,000 g/mol), 20% of electron conductor (EL1 and EL2, both from Merck), 30% of a wide band gap triplet matrix (TMM-004 from Merck) and 20% of hole conductor. The hole conductor employed is on the one hand the 4,4'-linked compound (in accordance with Example 4), and on the other hand the corresponding 2,2'-linked compound. The results are shown in Table 1. The hole conductors used (2,2'-linked in accordance with the prior art and 4,4'-linked as compound according to the invention) are depicted below for clarity:

TABLE 1

|  | Electron conductor | Hole conductor | Max. eff. [cd/A] |
|---|---|---|---|
| Comparative Example 1 | EL1 | 2,2' | 27.4 cd/A |
| Example 8 | EL1 | 4,4' | 29.4 cd/A |
| Comparative Example 2 | EL2 | 2,2' | 12.7 cd/A |
| Example 9 | EL2 | 4,4' | 20.7 cd/A |

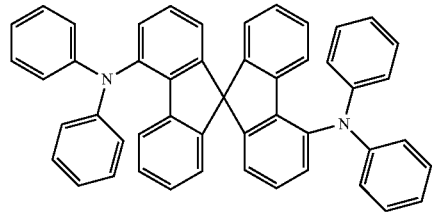

4,4'

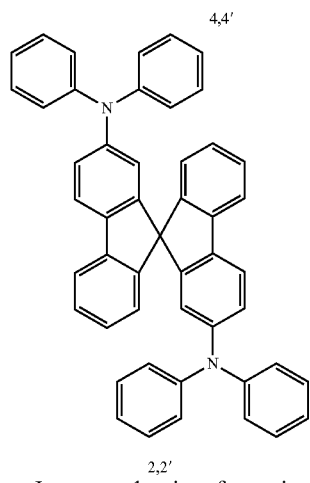

2,2'

In a second series of experiments (Examples 10 and 11 and Comparative Examples 3 and 4), the emitter concentration in the layer is increased to 20% by weight. Otherwise, the device structure is identical to that in Examples 8 and 9 and Comparative Examples 1 and 2. Due to the higher emitter concentration, the probability that the emitter is located in the direct vicinity of a quenching molecule also increases. In accordance with expectations, the influence on the efficiencies which can be achieved with the 4,4'-building blocks has consequently likewise increased. The results for this increased emitter concentration are shown in Table 2.

TABLE 2

|  | Electron conductor | Hole conductor | Max. eff. [cd/A] |
|---|---|---|---|
| Comparative Example 3 | EL1 | 2,2' | 15.4 cd/A |
| Example 10 | EL1 | 4,4' | 23.5 cd/A |
| Comparative Example 4 | EL2 | 2,2' | 18.7 cd/A |
| Example 11 | EL2 | 4,4' | 24.5 cd/A |

In a third series of experiments (Example 12 and Comparative Example 5), an electron conductor in the 4,4'-configuration (in accordance with Example 7) is compared with one in the 2,2'-configuration instead of the hole conductor. Since no hole conductor is employed in this case, an interlayer (HIL-012 from Merck) is used. Apart from the triplet emitter (TEG, 20% by weight, as in the preceding examples), the EML also again comprised a wide band gap matrix (TMM, from Merck) and polystyrene as binder. Since in this case the triplet layer is not in direct contact with the PEDOT, the lifetime is also measured here. Otherwise, the device structure is identical to that in the examples given above. It is apparent here that the use of the 4,4'-linked materials also has an advantageous effect on this important parameter. The results of this series of experiments are shown in Table 3. The electron conductors used (2,2'-linked in accordance with the prior art and 4,4'-linked as compound according to the invention) are depicted below for clarity:

TABLE 3

|  | Electron conductor | Max. eff. [cd/A] | Lifetime @ 1000 cd/m$^2$ |
|---|---|---|---|
| Comparative Example 5 | 2,2' | 20.5 cd/A | 3200 h |
| Example 12 | 4,4' | 22.7 cd/A | 4500 h |

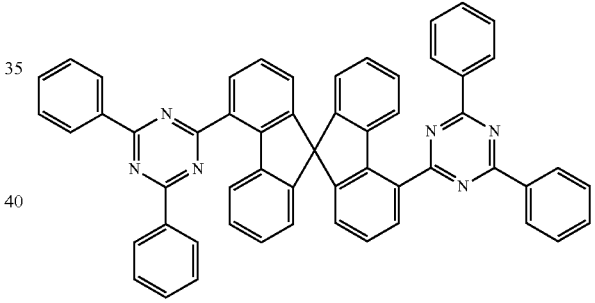

4,4'

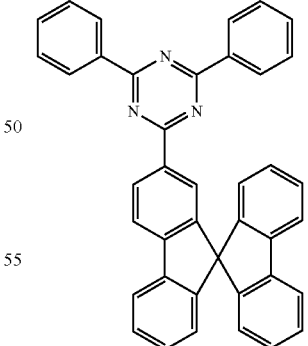
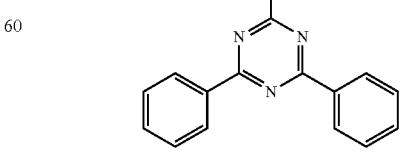

2,2'

The invention claimed is:
1. A compound of formula I

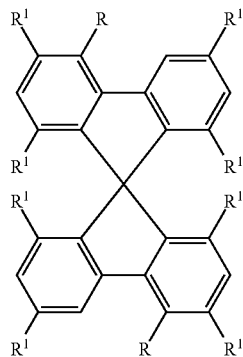

formula I wherein
R is selected on each occurrence, identically or differently, from the group consisting of F, CN, NO$_2$, ArNAr$_2$, NAr$_2$, C(=O)Ar, C(=O)R$^2$, P(=O)Ar$_2$, S(=O)Ar, S(=O)$_2$Ar, —CR$^2$=C(R$^2$)$_2$ and a mono- or polycyclic aromatic or heteroaromatic ring system having 5 to 60 aromatic ring atoms, optionally substituted by one or more non-aromatic radicals R$^1$; two radicals Ar which are bonded to the same nitrogen or phosphorus atom are optionally linked to one another by a single bond or a bridge selected from B(R$^2$), C(R$^2$)$_2$, Si(R$^2$)$_2$, C=O, C=NR$^2$, C=C(R$^2$)$_2$, O, S, S=O, SO$_2$, N(R$^2$), P(R$^2$) and P(=O)R$^2$;
R$^1$ is selected, identically or differently on each occurrence, from the group consisting of H, D, F, OH, CN, a straight-chain alkyl, alkoxy or thioalkoxy group having 1 to 40 C atoms and a branched or cyclic alkyl, alkoxy or thioalkoxy group having 3 to 40 C atoms or an alkenyl group having 2 to 40 C atoms, each of which is optionally substituted by one or more radicals R$^2$, where one or more non-adjacent CH$_2$ groups is optionally replaced by R$^2$C=CR$^2$, C≡C, Si(R$^2$)$_2$, C=O, C=S, C=NR$^2$, P(=O)(R$^2$), SO, SO$_2$, NR$^2$, O or S and where one or more H atoms is optionally replaced by D, F, Cl, Br, I, CN or NO$_2$; where, in addition, the respective R$^1$ which is located in the vicinal position to the radical R, in the case where R is an aromatic or heteroaromatic ring system, is optionally a divalent unit which is linked to the group R;
Ar is on each occurrence, identically or differently, an aromatic or heteroaromatic ring system having 5 to 30 aromatic ring atoms, which may be substituted by one or more radicals R$^1$;
R$^2$ is selected on each occurrence, identically or differently, from the group consisting of H, D, F, CN and an aliphatic, aromatic or heteroaromatic hydrocarbon radical having 1 to 20 C atoms, in which, in addition, one or more H atoms may be replaced by F, CN, a straight-chain alkyl, alkoxy or thioalkoxy group having 1 to 40 C atoms or a branched or cyclic alkyl, alkoxy or thioalkoxy group having 3 to 40 C atoms; two or more adjacent substituents R$^2$ may also be linked to one another by a covalent bond or also, in the case where the R$^2$ involved are aromatic or heteroaromatic hydrocarbon radicals, by one or more divalent aliphatic hydrocarbon units.

2. The compound of claim 1, wherein R is selected from the group consisting of NAr$_2$, C(=O)R$^2$, CR$^2$=CR$^2$$_2$ and a mono- or polycyclic aromatic or heteroaromatic ring system having 5 to 40 aromatic ring atoms, optionally substituted by one or more non-aromatic radicals R$^1$; where, in addition, two radicals Ar which are bonded to the same nitrogen atom are optionally linked to one another by a single bond or a bridge selected from C(R$^2$)$_2$, C=O, O, S and N(R$^2$).

3. The compound of claim 1, wherein R is on each occurrence, identically or differently, NAr$_2$ or a mono- or polycyclic aromatic or heteroaromatic ring system having 5 to 20 aromatic ring atoms.

4. The compound of claim 1, wherein R is selected, identically or differently, from the group consisting of the following radicals:

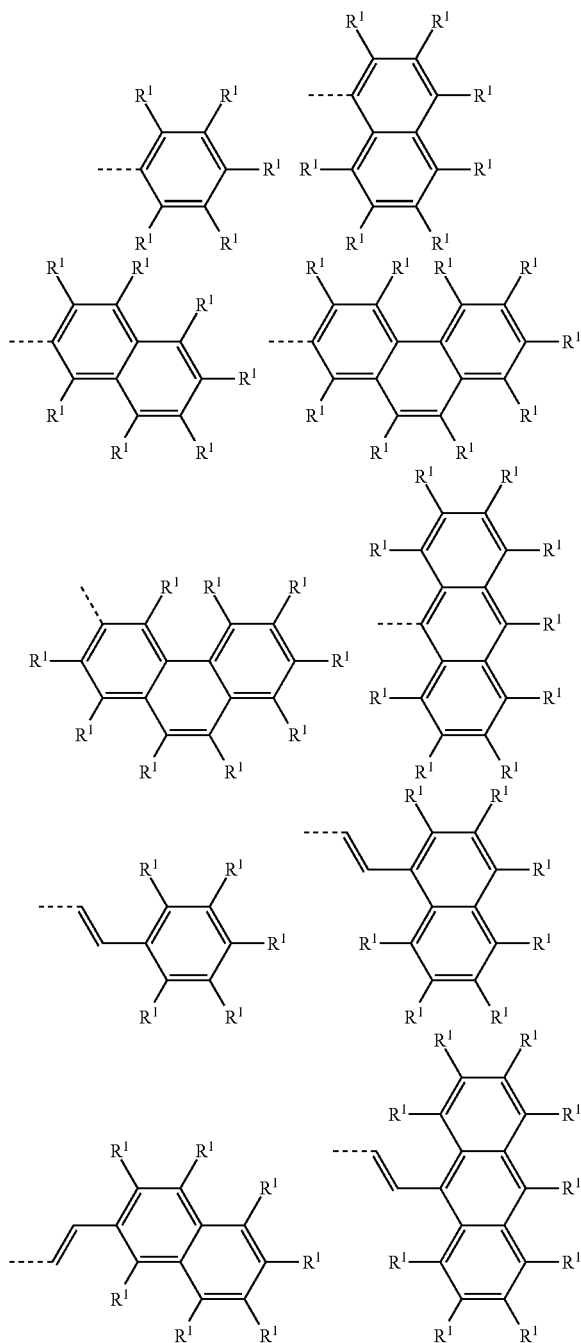

-continued

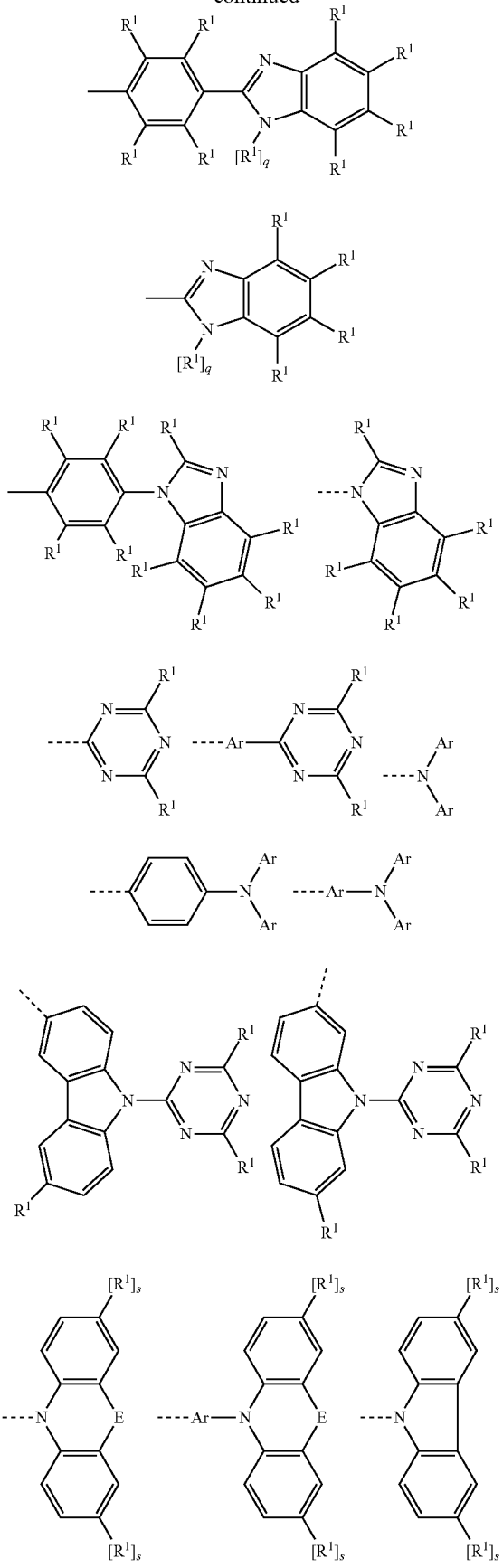

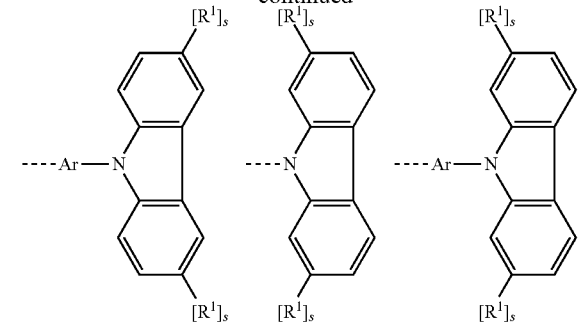

where the dashed line in the groups is intended to indicate that the group is bonded at this position, and where s and q are each, independently of one another, 0 or 1, where, for s=0 or q=0, the R¹ in question is replaced by an H, and E is selected from the group consisting of C(R¹)₂, NR¹, O, C=O, S, S=O and S(O)₂.

5. The compound of claim 1, wherein R¹ is selected, identically or differently on each occurrence, from the group consisting of H, D, F, CN, a straight-chain alkyl, alkoxy or thioalkoxy group having 1 to 20 C atoms and a branched or cyclic alkyl, alkoxy or thioalkoxy group having 3 to 20 C atoms; where, in addition, the respective R¹ which is located in the vicinal position to the radical R is optionally a divalent unit, which is optionally linked to the aromatic or heteroaromatic ring system of the group R.

6. The compound of claim 1, wherein Ar is an aromatic or heteroaromatic ring system having 5 to 14 aromatic ring atoms.

7. The compound of claim 1, wherein said compound is a compound of formula II or III:

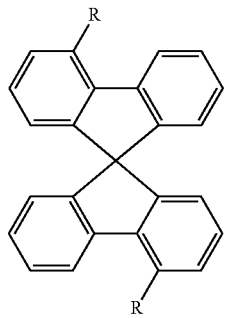

formula (II)

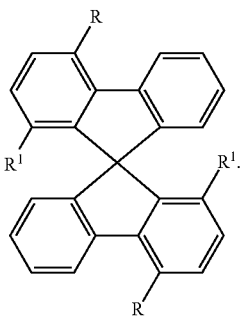

formula (III)

8. A process for preparing the compound of claim 1 comprising the step of coupling a spirobifluorene or a spirobifluorene derivative which is substituted in the 4,4'-position by a reactive leaving group to a functionalised aromatic compound or to a mono- or disubstituted amine.

9. A mixture comprising at least one compound according to claim 1 and at least one further compound.

10. A formulation or solution comprising at least one compound according to claim 1 and at least one solvent.

11. An electronic device comprising at least one compound according to claim 1.

12. The electronic device of claim 11, wherein said electronic device is selected from the group consisting of organic electroluminescent devices, organic field-effect transistors, organic thin-film transistors, organic light-emitting transistors, organic integrated circuits, organic solar cells, organic field-quench devices, light-emitting electrochemical cells, organic laser diodes, and organic photoreceptors.

13. The electronic device of claim 12, wherein said electronic device is an organic electroluminescent device, and wherein the at least one compound of claim 1 is employed as host material for fluorescent or phosphorescent dopants.

14. The electronic device of claim 12, wherein said electronic device is an organic electroluminescent device, and wherein the at least one compound of claim 1 is employed as emitting material, as hole-transport material, as hole-injection material, or as electron-transport material.

15. The compound of claim 1, wherein $R^1$ is selected, identically or differently, from the group consisting of H, D, F, and CN.

16. The compound of claim 1, wherein $R^1$ is in each case hydrogen.

17. A formulation or solution comprising at least one mixture according to claim 9 and at least one solvent.

18. An electronic device comprising at least one mixture according to claim 9.

19. An electronic device comprising at least one solution or formulation according to claim 10.

* * * * *